(12) United States Patent
Brady et al.

(10) Patent No.: US 9,259,737 B2
(45) Date of Patent: *Feb. 16, 2016

(54) LAB MEMBERS AND LIQUID HANDLING SYSTEMS AND METHODS INCLUDING SAME

(71) Applicant: PERKINELMER HEALTH SCIENCES, INC., Waltham, MA (US)

(72) Inventors: Lee Brady, Downers Grove, IL (US); Larry Schoell, Shorewood, IL (US); Gary Millard, Lisle, IL (US); Richard R. Harazin, Lombard, IL (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/313,467

(22) Filed: Jun. 24, 2014

(65) Prior Publication Data

US 2014/0305229 A1    Oct. 16, 2014

Related U.S. Application Data

(63) Continuation of application No. 13/475,563, filed on May 18, 2012, now Pat. No. 8,809,069.

(60) Provisional application No. 61/488,529, filed on May 20, 2011.

(51) Int. Cl.
*G01N 35/10* (2006.01)
*B01L 9/04* (2006.01)
(Continued)

(52) U.S. Cl.
CPC ............... *B01L 9/54* (2013.01); *B01L 3/021* (2013.01); *G01N 35/1065* (2013.01); *G01N 2035/1051* (2013.01); *Y10T 137/0329* (2015.04); *Y10T 436/2575* (2015.01)

(58) Field of Classification Search
CPC ........... B01L 3/021; B01L 9/54; B01L 9/543; B01L 2300/06; B01L 2300/0609; G01N 2035/1051; G01N 35/1065
See application file for complete search history.

(56) References Cited

U.S. PATENT DOCUMENTS 3,444,742 A    5/1969  Ellis et al.
3,657,694 A    4/1972  Lindsey
(Continued)

FOREIGN PATENT DOCUMENTS

EP    0571100 A1    11/1993
EP    1443330 A1    8/2004
(Continued)

OTHER PUBLICATIONS

International Search Report Corresponding to International Application No. PCT/2013/034146; Date of Mailing: Oct. 1, 2014 (8 pgs).
(Continued)

*Primary Examiner* — Brian R Gordon
(74) *Attorney, Agent, or Firm* — Myers Bigel Sibley & Sajovec, PA

(57) ABSTRACT

A lab member for use in a laboratory liquid handling system including a pipetting module and a drive system, the pipetting module including first and second pipettors, the first and second pipettors including first and second pipettor shafts, respectively, a first pipetting tip extending from an end of the first pipettor shaft, and a second pipetting tip extending from an end of the second pipettor shaft, includes a lab object and first and second integral adapter structures. The first and second adapter structures are configured to engage the first and second pipettor shafts, respectively. The first adapter structure is configured to releasably secure the lab member to the first pipettor shaft.

22 Claims, 28 Drawing Sheets

(51) Int. Cl.
  *B01L 9/00* (2006.01)
  *B01L 3/02* (2006.01)

(56) References Cited

U.S. PATENT DOCUMENTS

| | | | |
|---|---|---|---|
| 3,855,868 | A | 12/1974 | Sudvaniemi |
| 4,389,374 | A | 6/1983 | Sutton et al. |
| 4,830,832 | A | 5/1989 | Arpagaus et al. |
| 5,365,783 | A | 11/1994 | Zweifel |
| 5,487,997 | A | 1/1996 | Stolp |
| 5,496,473 | A | 3/1996 | Chow |
| 5,525,302 | A | 6/1996 | Astle |
| 5,651,941 | A | 7/1997 | Stark et al. |
| 5,916,527 | A | 6/1999 | Haswell |
| 5,961,927 | A | 10/1999 | Isaacs et al. |
| 6,019,225 | A | 2/2000 | Kalmakis et al. |
| 6,156,275 | A | 12/2000 | Dumitrescu et al. |
| 6,182,719 | B1 | 2/2001 | Yahiro |
| 6,203,760 | B1 | 3/2001 | van der Plaats et al. |
| 6,253,807 | B1 | 7/2001 | Jones |
| 6,417,007 | B1 | 7/2002 | Gittleman et al. |
| 6,589,483 | B1 | 7/2003 | Maeda |
| 7,018,587 | B2 | 3/2006 | Heath et al. |
| 7,169,361 | B2 | 1/2007 | Arnold et al. |
| 7,191,647 | B2 | 3/2007 | Harazin et al. |
| 7,220,590 | B2 | 5/2007 | Moritz et al. |
| 7,314,598 | B2 | 1/2008 | Nishino |
| 7,411,508 | B2 | 8/2008 | Harazin et al. |
| 7,513,857 | B2 | 4/2009 | Gueller et al. |
| 7,635,326 | B2 | 12/2009 | Gueller et al. |
| 7,858,041 | B2 | 12/2010 | Muraishi et al. |
| 8,021,611 | B2 | 9/2011 | Roach et al. |
| 8,057,756 | B2 | 11/2011 | Londo et al. |
| 8,192,698 | B2 | 6/2012 | Londo et al. |
| 8,287,820 | B2 | 10/2012 | Williams et al. |
| 8,377,396 | B2 * | 2/2013 | Meinicke ............... B25J 15/00 422/500 |
| 8,398,941 | B2 | 3/2013 | Sinclair et al. |
| 9,073,052 | B2 * | 7/2015 | Maslana ............... B01L 3/021 |
| 2001/0028863 | A1 | 10/2001 | Kitagawa |
| 2002/0095998 | A1 | 7/2002 | Kriz et al. |
| 2003/0017084 | A1 | 1/2003 | Dale et al. |
| 2003/0215365 | A1 | 11/2003 | Sevigny et al. |
| 2004/0067170 | A1 | 4/2004 | Higuchi |
| 2004/0069076 | A1 | 4/2004 | Gamble |
| 2004/0070225 | A1 | 4/2004 | Meincke et al. |
| 2006/0093530 | A1 | 5/2006 | Ueda |
| 2007/0269853 | A1 | 11/2007 | Galiano |
| 2009/0129978 | A1 | 5/2009 | Wilson et al. |
| 2010/0226828 | A1 | 9/2010 | Itoh |
| 2010/0313688 | A1 | 12/2010 | Hiltbrand |
| 2013/0259635 | A1 | 10/2013 | Masiana et al. |

FOREIGN PATENT DOCUMENTS

| | | |
|---|---|---|
| GB | 2431600 A | 5/2007 |
| KR | 790001034 B1 | 8/1979 |
| WO | WO 00/08472 A2 | 2/2000 |
| WO | WO 00/25922 A2 | 5/2000 |
| WO | WO 2005/059567 A1 | 6/2005 |
| WO | WO 2006/083695 A2 | 8/2006 |

OTHER PUBLICATIONS

European Examination Report Corresponding to European Application No. 12726279.8; Dated: Jul. 2, 2015; 4 Pages.
Flaherty, N. (Apr. 23, 2009), JANUS Product Portfolio. PerkinElmer (26 pages).
"Hamilton Robotics: Labware Manipulation Tools," Hamilton Robotics, Retrieved Date: May 3, 2012, From URL: http://www.hamliltonrobotics.com/hamilton-robotics/liquidhandling/star/labware-manipulation-tools/ (3 pages).
"Hamilton Robotics: Microplate Gripping CO-RE Grip," Hamilton Robotics, Retrieved Date: May 3, 2012, From URL: http://www.hamiltonrobotics.com/hamilton-robotics/liquidhandling/star/labware-manipulation-tools/microplate-co-re-grip/ (2 pages).
"Hamilton Robotics: eSWAP Gripper," Hamilton Robotics, Retrieved Date: May 3, 2012, From URL: http://www.hamiltonrobotics.com/hamilton-robotics/liquidhandling/star/labware-manipulation-tools/swap-external-gripper/ (4 pages).
"Hamilton Robotics: iSWAP Microplate Gripper," Hamilton Robotics, Retrieved Date: May 3, 2012, From URL: http://www.hamiltonrobotics.com/hamilton-robotics/liquidhandling/star/labware-manipulation-tools/iswap-microplate-gripper/ (3 pages).
"JANUS® Automated Workstation from PerkinElmer—USA," PerkinElmer, Inc., Retrieved Date: Feb. 9, 2011, From URL: las.perkinelmer.com/Catalog/CategoryPage.htm?CategoryID=JANUS (2 pages).
Notification Concerning Transmittal of International Preliminary Report on Patentability for corresponding PCT Application No. PCT/US2012/038520 mailed Nov. 28, 2013 (10 pages).
"Plate-GripX" Xiral, Retrieved Date: Feb. 9, 2011, From URL: http://www.xiril.com/xiril/printable/products/optionsaccessories/plategripx/index.html (1 page).
"SPE Module—automated vacuum extraction" Xiral, Retrieved Date: May 3, 2012, From URL: http://www.xiril.com/xiril/printable/products/optionsaccessories/spemodule/index.html (1 page).
"VERSA Liquid Handling Systems Accessories & Modules" Aurora Biomed, Retrieved Date: Feb. 21, 2011, From URL: http://aurorabiomed.com/liquid-handling-accessories.htm (3 pages).
"Waters: Lid Assembly [M880877BC1]," Waters, Retrieved Date: Apr. 8, 2011, From URL: http://waters.com/waters/partDetail.htm?locale=en_US&partNumber=M880877BC1 (1 page).

* cited by examiner

LAB MEMBERS AND LIQUID HANDLING SYSTEMS AND METHODS INCLUDING SAME

RELATED APPLICATION(S)

The present application is a continuation application of and claims priority from U.S. patent application Ser. No. 13/475,563 filed May 18, 2012, issued as U.S. Pat. No. 8,809,069, which claims the benefit of and priority from U.S. Provisional Patent Application No. 61/488,529, filed May 20, 2011, the disclosures of which are incorporated herein by reference in their entireties.

FIELD

The present invention relates to laboratory liquid handling systems and, more particularly, to lab members for use in laboratory liquid handling systems and laboratory liquid handling systems and methods incorporating the same.

BACKGROUND

Laboratory liquid handling systems are used to transport and operate on volumes of liquid. For example, one or more liquid samples may be provided in containers (e.g., microwell plates or vials) in a liquid handling system. The liquid handling system may include one or more pipettors that are used to remove (e.g., by aspirating) portions of the samples from the containers and/or to add (e.g., by dispensing) material to the samples in the containers. In some cases, it may be desirable or necessary to move labware or tools within the system. For example, it may be desired to place a lid on a container, to remove a lid from a container, or to move a container (e.g., to a heating station, agitator or sensor). It may be desirable or necessary to execute the aforedescribed procedures robotically and, in some cases, automatically and programmatically.

SUMMARY

According to embodiments of the present invention, a lab member for use in a laboratory liquid handling system including a pipetting module and a drive system, the pipetting module including first and second pipettors, the first and second pipettors including first and second pipettor shafts, respectively, a first pipetting tip extending from an end of the first pipettor shaft, and a second pipetting tip extending from an end of the second pipettor shaft, includes a lab object and first and second integral adapter structures. The first and second adapter structures are configured to engage the first and second pipettor shafts, respectively. The first adapter structure is configured to releasably secure the lab member to the first pipettor shaft.

According to some embodiments, the first adapter structure is configured to snugly couple with the first pipettor shaft to support the lab member during transport on the pipetting module, and the second adapter structure is configured to loosely couple with the second pipettor shaft.

In some embodiments, the first and second adapter structures are configured to snugly couple with the first and second pipettor shafts to secure the lab member to the pipetting module during transport on the pipetting module.

The lab member may further include a third integral adapter structure configured to engage a third pipettor shaft of the pipetting module. The third adapter structure is configured to releasably secure the lab member to the third pipettor shaft.

According to some embodiments, the lab object is a lab tool and/or labware. In some embodiments, the lab object is a lid. In some embodiments, the lab object is a receptacle carrier. In some embodiments, the lab object is a filter disk assembly. In some embodiments, the lab object includes an electronics module. The lab member may be configured to transmit power and/or communications signals through at least one of the first and second integral adapter structures to and/or from the electronics module. In some embodiments, the lab object is a sensor module. In some embodiments, the lab object includes an atomizer.

According to some embodiments, at least one of the first and second adapter structures is removably and replaceably secured to the lab object.

According to embodiments of the present invention, a laboratory liquid handling system includes a pipetting module, a lab member and a drive system. The pipetting module includes first and second pipettors. The first and second pipettors include first and second pipettor shafts, respectively. A first pipetting tip extends from an end of the first pipettor shaft. A second pipetting tip extends from an end of the second pipettor shaft. The lab member includes a lab object and first and second integral adapter structures configured to engage the first and second pipettor shafts, respectively. The first adapter structure is configured to releasably secure the lab member to the first pipettor shaft. The drive system is operable to: selectively engage the first pipettor shaft with the first adapter structure to secure the lab member to the pipetting module; selectively engage the second pipettor shaft with the second adapter structure; move the pipetting module to transport the lab member secured thereto; and selectively disengage the first pipettor shaft from the first adapter structure to thereby release the lab member from the pipetting module.

In some embodiments, the first adapter structure is configured to snugly couple with the first pipettor shaft to support the lab member during transport on the pipetting module, and the second adapter structure is configured to loosely couple with the second pipettor shaft.

According to some embodiments, the first and second adapter structures are configured to snugly couple with the first and second pipettor shafts to secure the lab member to the pipetting module during transport on the pipetting module.

According to some embodiments, the pipetting module further includes a third pipettor, the third pipettor including a third pipettor shaft and a third pipetting tip extending from an end of the third pipettor shaft, and the lab member further includes a third integral adapter structure configured to engage the third pipettor shaft. The third adapter structure is configured to releasably secure the lab member to the third pipettor shaft. The drive system is operable to: selectively engage the third pipettor shaft with the third adapter structure to secure the lab member to the pipetting module; and selectively disengage the third pipettor shaft from the third adapter structure to thereby release the lab member from the pipetting module.

In some embodiments, the drive system further includes an ejector mechanism on the first pipettor shaft operable to disengage the first adapter structure from the first pipettor shaft.

According to some embodiments, the lab object is a lab tool and/or labware. In some embodiments, the lab object is selected from the group consisting of a lid, a receptacle carrier, a filter disk assembly, and a sensor module.

According to method embodiments of the present invention, a method for transporting a lab member using a laboratory liquid handling system including a pipetting module and a drive system, the pipetting module including first and second pipettors, the first and second pipettors including first and second pipettor shafts, respectively, a first pipetting tip extending from an end of the first pipettor shaft, and a second pipetting tip extending from an end of the second pipettor shaft, includes providing a lab member. The lab member includes a lab object and first and second integral adapter structures configured to engage the first and second pipettor shafts, respectively. The first adapter structure is configured to releasably secure the lab member to the first pipettor shaft. The method further includes, using the drive system: selectively engaging the first pipettor shaft with the first adapter structure to secure the lab member to the pipetting module; selectively engaging the second pipettor shaft with the second adapter structure; moving the pipetting module to transport the lab member secured thereto; and selectively disengaging the first pipettor shaft from the first adapter structure to thereby release the lab member from the pipetting module.

In some embodiments, disengaging the first pipettor shaft from the first adapter structure includes axially withdrawing the first pipettor shaft from the first adapter structure while engaging the second adapter structure with the second pipettor shaft to resist axial displacement of the lab member.

According to embodiments of the present invention, a lab member for use in a laboratory liquid handling system including a pipetting module and a drive system, the pipetting module including a pipettor, the pipettor including a pipettor shaft and a pipetting tip extending from an end of the pipettor shaft, includes a lab object and an integral adapter structure. The adapter structure is configured to releasably secure the lab member to the pipettor shaft. The adapter structure includes a clamping mechanism configured to releasably grasp the pipettor shaft.

In some embodiments, the clamping mechanism includes a sleeve configured to receive the pipettor shaft. The sleeve has an expansion slot defined therein to permit radial expansion of the sleeve. According to some embodiments, the adapter structure includes an interlock structure on the sleeve arranged and configured to releasably interlock with an interlock structure on the pipettor shaft when the pipettor shaft is engaged with the adapter structure to secure the lab member to the pipetting module.

According to some embodiments, the lab object includes a pin tool.

According to embodiments of the present invention, a laboratory liquid handling system includes a pipetting module, a lab member, and a drive system. The pipetting module includes a pipettor. The pipettor includes a pipettor shaft and a pipetting tip extending from an end of the pipettor shaft. The lab member includes a lab object and an integral adapter structure. The adapter structure is configured to releasably secure the lab member to the pipettor shaft. The drive system is operable to: selectively engage the pipettor shaft with the adapter structure to secure the lab member to the pipetting module; move the pipetting module to transport the lab member secured thereto; and selectively disengage the pipettor shaft from the adapter structure to thereby release the lab member from the pipetting module. The adapter structure includes a clamping mechanism configured to releasably grasp the pipettor shaft.

In some embodiments, the clamping mechanism includes a sleeve configured to receive the pipettor shaft. The sleeve has an expansion slot defined therein to permit radial expansion of the sleeve.

According to some embodiments, the laboratory liquid handling system includes a first interlock structure on the pipettor shaft and a second interlock structure on the sleeve. The first and second interlock structures are arranged and configured to releasably interlock with one another when the pipettor shaft is engaged with the adapter structure to secure the lab member to the pipetting module.

According to method embodiments of the present invention, a method for transporting a lab member using a laboratory liquid handling system including a pipetting module and a drive system, the pipetting module including a pipettor, the pipettor including a pipettor shaft and a pipetting tip extending from an end of the pipettor shaft, includes providing a lab member. The lab member includes a lab object and an integral adapter structure. The adapter structure is configured to releasably secure the lab member to the pipettor shaft. The adapter structure includes a clamping mechanism configured to releasably grasp the pipettor shaft. The method further includes engaging the pipettor with the adapter structure such that the clamping mechanism releasably grasps the pipettor shaft to secure the lab member to the pipettor.

According to embodiments of the present invention, a lab member for use in a laboratory liquid handling system including a pipetting module and a drive system, the pipetting module including a pipettor, the pipettor including a pipettor shaft and a pipetting tip extending from an end of the pipettor shaft, includes a lab object and an integral adapter structure. The adapter structure is configured to releasably secure the lab member to the pipettor shaft. The adapter structure includes an interlock structure arranged and configured to releasably interlock with an interlock structure on the pipettor shaft when the pipettor shaft is engaged with the adapter structure to secure the lab member to the pipetting module.

According to embodiments of the present invention, a laboratory liquid handling system includes a pipetting module, a lab member and a drive system. The pipetting module includes a pipettor. The pipettor includes a pipettor shaft, a pipetting tip extending from an end of the pipettor shaft, and a first interlock structure on the pipettor shaft. The lab member includes a lab object and an integral adapter structure. The adapter structure includes a second interlock structure and is configured to releasably secure the lab member to the pipettor shaft. The drive system is operable to: selectively engage the pipettor shaft with the adapter structure to secure the lab member to the pipetting module; move the pipetting module to transport the lab member secured thereto; and selectively disengage the pipettor shaft from the adapter structure to thereby release the lab member from the pipetting module. The first and second interlock structures are arranged and configured to releasably interlock with one another when the pipettor shaft is engaged with the adapter structure to secure the lab member to the pipetting module.

According to method embodiments of the present invention, a method for transporting a lab member using a laboratory liquid handling system including a pipetting module and a drive system, the pipetting module including a pipettor, the pipettor including a pipettor shaft and a pipetting tip extending from an end of the pipettor shaft, includes providing a lab member. The lab member includes a lab object and an integral adapter structure. The adapter structure is configured to releasably secure the lab member to the pipettor shaft. The adapter structure includes an interlock structure arranged and configured to releasably interlock with an interlock structure on the pipettor shaft. The method further includes engaging the pipettor with the adapter structure such that the interlock feature of the adapter structure releasably interlocks with the interlock structure on the pipettor shaft to secure the lab member to the pipetting module.

According to embodiments of the present invention, a lab member for use with a solid workpiece in a laboratory liquid handling system including a pipetting module and a drive system, the pipetting module including a pipettor, the pipettor including a pipettor shaft and a pipetting tip extending from an end of the pipettor shaft, includes a lab object, an integral adapter structure, and an integral holder structure. The adapter structure is configured to releasably secure the lab member to the pipettor shaft. The holder structure is configured to releasably secure the lab member to the solid workpiece.

According to embodiments of the present invention, a laboratory liquid handling system for use with a solid workpiece includes a pipetting module, a lab member and a drive system. The pipetting module includes a pipettor. The pipettor includes a pipettor shaft and a pipetting tip extending from an end of the pipettor shaft. The lab member includes a lab object, an integral adapter structure and an integral holder structure. The adapter structure is configured to releasably secure the lab member to the pipettor shaft. The holder structure is configured to releasably secure the lab member to the solid workpiece. The drive system is operable to: selectively engage the pipettor shaft with the adapter structure to secure the lab member to the pipetting module; move the pipetting module to transport the lab member secured thereto; and selectively disengage the pipettor shaft from the adapter structure to thereby release the lab member from the pipetting module.

According to method embodiments of the present invention, a method for moving a solid workpiece using a laboratory liquid handling system including a pipetting module and a drive system, the pipetting module including a pipettor, the pipettor including a pipettor shaft and a pipetting tip extending from an end of the pipettor shaft, includes providing a lab member. The lab member includes a lab object, an integral adapter structure, and an integral holder structure. The adapter structure is configured to releasably secure the lab member to the pipettor shaft. The holder structure is configured to releasably secure the lab member to the solid workpiece. The method further includes: engaging the pipettor with the adapter structure such that the adapter structure releasably secures the lab member to the pipettor shaft; and engaging the holder structure with the solid workpiece such that the holder structure releasably secures the solid workpiece to the lab member and thereby to the pipettor shaft.

According to embodiments of the present invention, a lab member for use in a laboratory liquid handling system including a pipetting module and a drive system, the pipetting module including a pipettor, the pipettor including a pipettor shaft and a pipetting tip extending from an end of the pipettor shaft, includes a pin tool and an integral adapter structure. The pin tool includes a tip configured to collect, hold and release a droplet from a liquid sample. The adapter structure is configured to releasably secure the lab member to the pipettor shaft.

The pin tool may include a body and a floating pin member that is slidably mounted in the body.

According to embodiments of the present invention, a lab member for use in a laboratory liquid handling system including a pipetting module and a drive system, the pipetting module including a pipettor, the pipettor including a pipettor shaft and a pipetting tip extending from an end of the pipettor shaft, includes an electronics module and an integral adapter structure. The adapter structure is configured to releasably secure the lab member to the pipettor shaft.

In some embodiments, the electronics module includes a sensor.

In some embodiments, the electronics module includes an electronic atomizer.

According to some embodiments, the lab member is configured to transmit power and/or communications signals through the integral adapter structure to and/or from the electronics module.

According to embodiments of the present invention, a lab member for use in a laboratory liquid handling system including a pipetting module and a drive system, the pipetting module including a pipettor, the pipettor including a pipettor shaft and a pipetting tip extending from an end of the pipettor shaft, includes an atomizer and an integral adapter structure. The adapter structure is configured to releasably secure the lab member to the pipettor shaft.

According to embodiments of the present invention, a lab member for use in a laboratory liquid handling system including a pipetting module and a drive system, the pipetting module including a pipettor, the pipettor including a pipettor shaft and a pipetting tip extending from an end of the pipettor shaft, includes a lab object and an integral adapter member. The adapter structure is configured to releasably secure the lab member to the pipettor shaft. The adapter structure is removably and replaceably secured to the lab object.

According to embodiments of the present invention, an auxiliary flowable material handling system for use in a laboratory liquid handling system including a pipetting module and a drive system, the pipetting module including a pipettor, the pipettor including a pipettor shaft and a pipetting tip extending from an end of the pipettor shaft, includes a material handler, a lab member, and a conduit. The lab member includes a nozzle and an integral adapter structure. The adapter structure is configured to releasably secure the lab member to the pipettor shaft. The conduit fluidly connects the material handler to the nozzle. The auxiliary flowable material handling system is operable to dispense a flowable material from the nozzle and/or to aspirate a flowable material into the nozzle.

In some embodiments, the nozzle includes a cannula configured to pierce a septa.

According to method embodiments of the present invention, a method for transporting a lab member using a laboratory liquid handling system including a pipetting module and a drive system, the pipetting module including a pipettor, the pipettor including a pipettor shaft and a pipetting tip extending from an end of the pipettor shaft, includes providing a sensor lab member including: a sensor module; and an integral adapter structure, wherein the adapter structure is configured to releasably secure the sensor lab member to the pipettor shaft. The method further includes: engaging the pipettor with the adapter structure to secure the sensor lab member to the pipettor; moving the pipetting module to transport the sensor lab member secured thereto to a selected location; using the sensor lab member, sensing an attribute at the desired location and generating and sending a corresponding data signal to a controller; and using the controller, programmatically determining a next action based on the data signal.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DESCRIPTION OF EMBODIMENTS OF THE INVENTION

Figure 1:
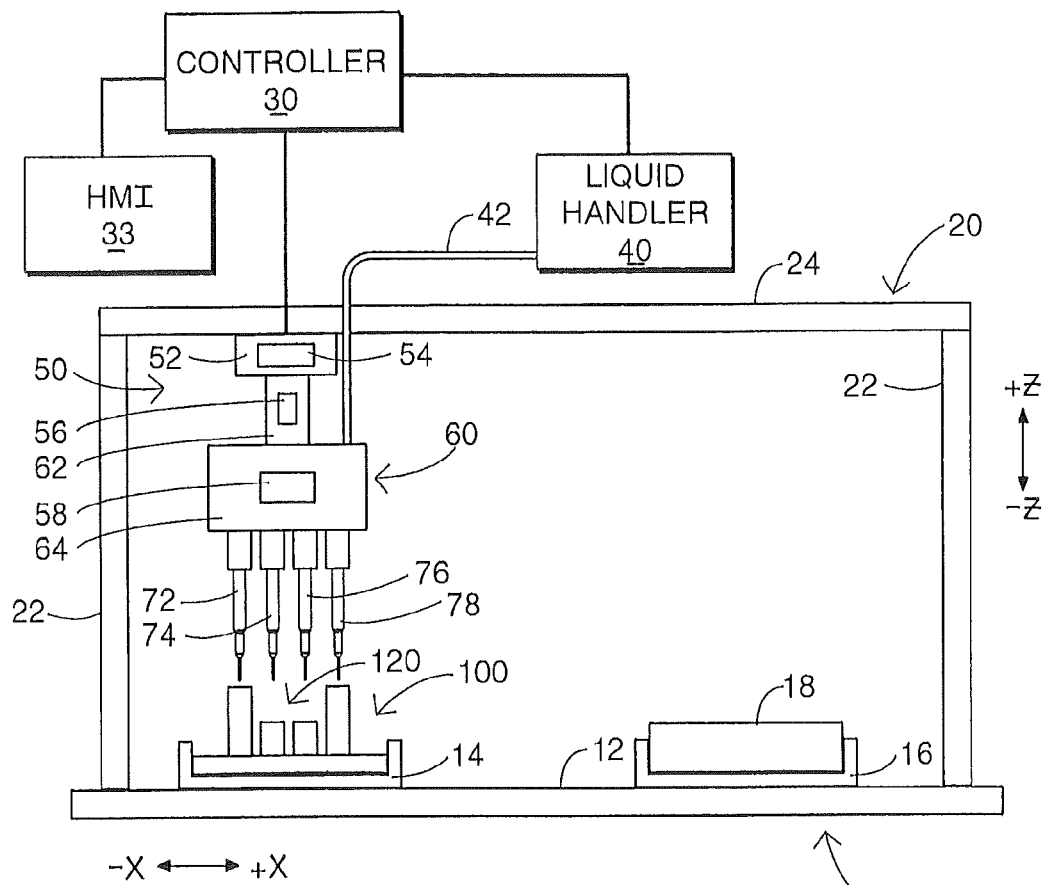
FIG. 1 is a schematic diagram of a laboratory liquid handling system according to embodiments of the present invention and including a pipetting module and a lab member according to embodiments of the present invention.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

The term "automatically" means that the operation is substantially, and may be entirely, carried out without human or manual input, and can be programmatically directed or carried out.

The term "programmatically" refers to operations directed and/or primarily carried out electronically by computer program modules, code and/or instructions.

The term "electronically" includes both wireless and wired connections between components.

The term "monolithic" means an object that is a single, unitary piece formed or composed of a material without joints or seams.

With reference to FIGS. 1-9, a lab member 100 according to embodiments of the present invention is shown therein. The lab member 100 forms a part of a laboratory liquid handling system 10 according to embodiments of the present invention.

With reference to FIG. 1, the system 10 as illustrated includes a platform or deck 12, a frame 20, a controller 30, a human machine interface (HMI) 33, a liquid handler 40, a drive system 50, and a pipetting gantry or module 60. A container 18 is disposed on the deck 12. The container 18 may include, for example, a microwell plate or a rack containing one or more vials. The container 18 may be located in a container rack or holder 16. A lid rack or holder 14 may also be provided on the deck 12.

The frame 20 includes supports 22 and one or more conveyor rails 24. The drive system 50 includes a shuttle or carrier 52 operatively mounted on the rail(s) 24 to enable the carrier 52 to move relative to the deck 12. According to some embodiments, the carrier 52 has freedom of movement in at least two lateral degrees (i.e., in an X dimension and a Y dimension). The pipetting module 60 is coupled to and suspended from the carrier 52 by an extension arm 62 such that the pipetting module 60 moves with the carrier 52. The carrier 52 can be driven by a motor or motors 54 under the control of the controller 30. The pipetting module 60 can be further movable in a Z dimension by a motor or motors 56 under the control of the controller 30. A further motor or motors 58 under the control of the controller 30 may be provided to move or reposition further components of the pipetting module 60 as described below.

The liquid handler 40 may be any suitable apparatus that can aspirate and/or dispense a desired amount of a liquid from or into a container. The liquid handler 40 may include, for example, a syringe or pump fluidly connected to the pipetting module 60 by one or more lengths of tubing 42. The liquid handler 40 may be controlled by the controller 30.

Figure 3:
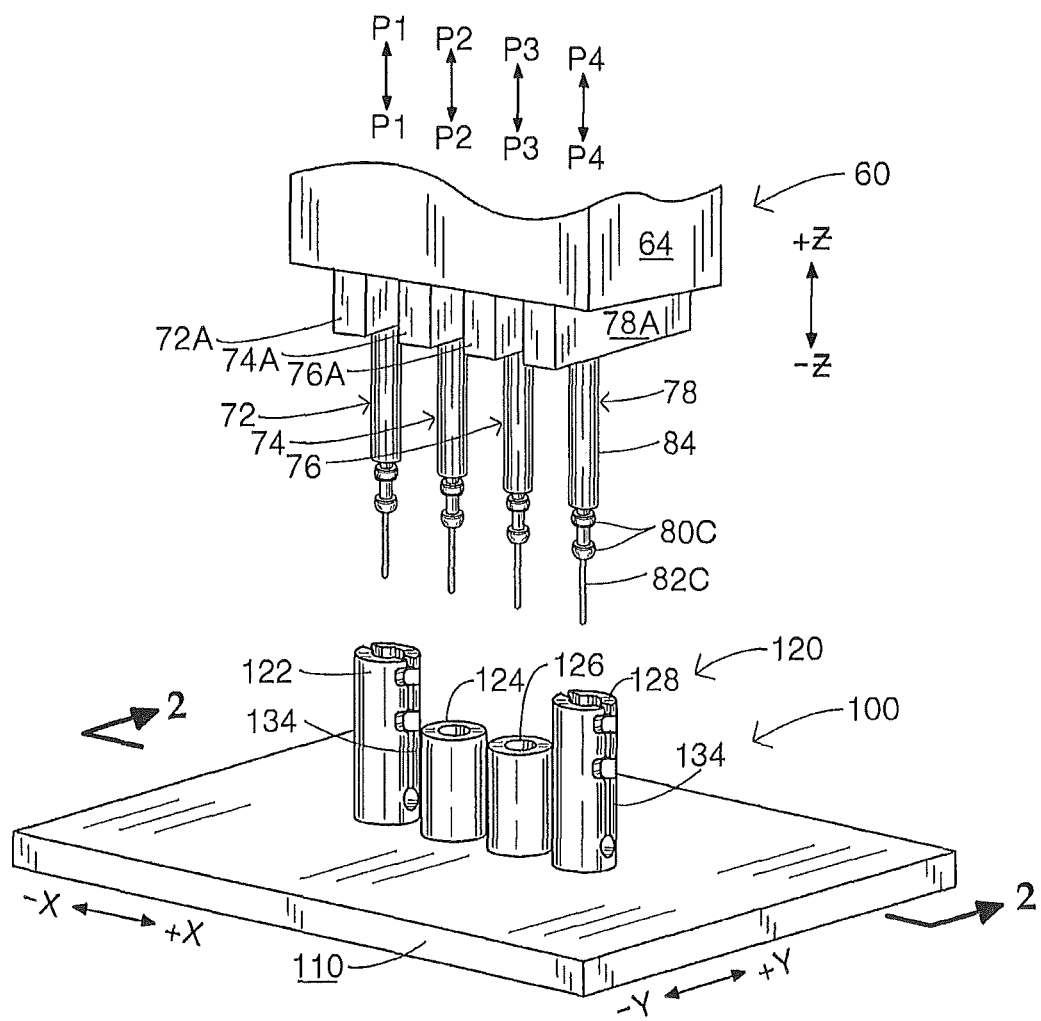
FIGS. 3-5 are fragmentary, perspective views of the laboratory liquid handling system of FIG. 1 illustrating a sequence of steps to mount the lab member of FIG. 1 on the pipetting module.
Figure 4:
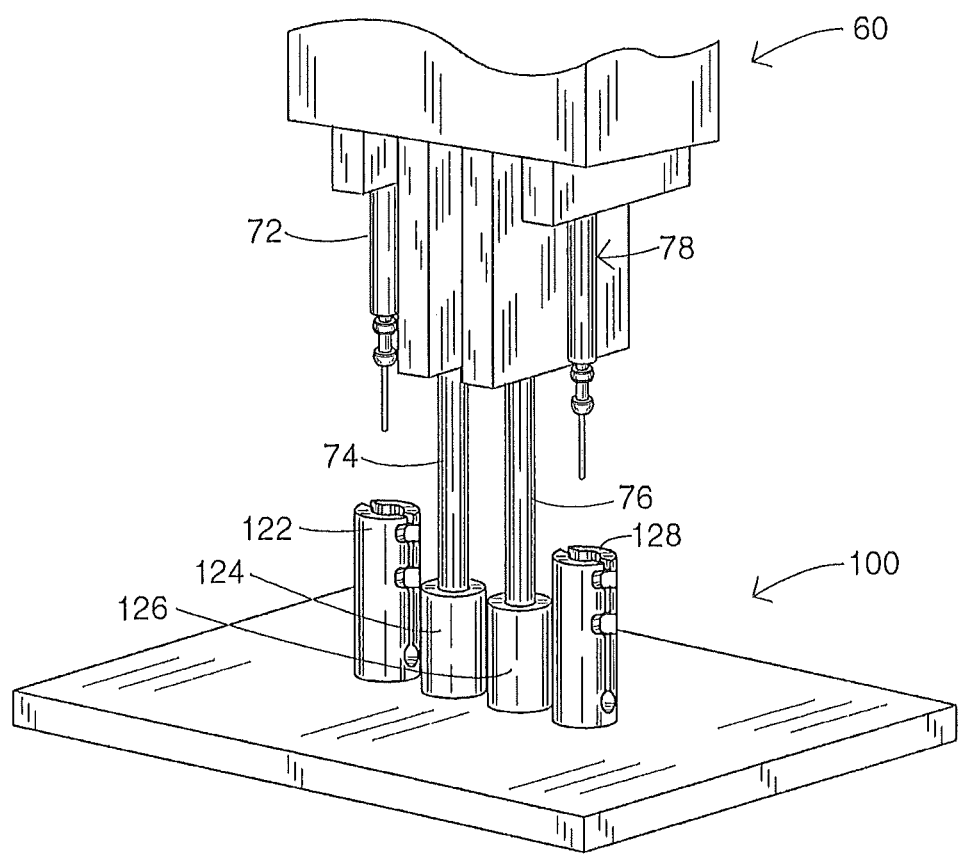

With reference to FIGS. 1 and 3, the pipetting module 60 includes a housing 64 connected to the lower end of the extension arm 62. The pipetting module 60 further includes four pipettors 72, 74, 76 and 78 each coupled to the housing 64 by a respective actuator assembly 72A, 74A, 76A, 78A. As discussed herein, pipetting modules having more or fewer pipettors may be employed in some embodiments.

Figure 7:
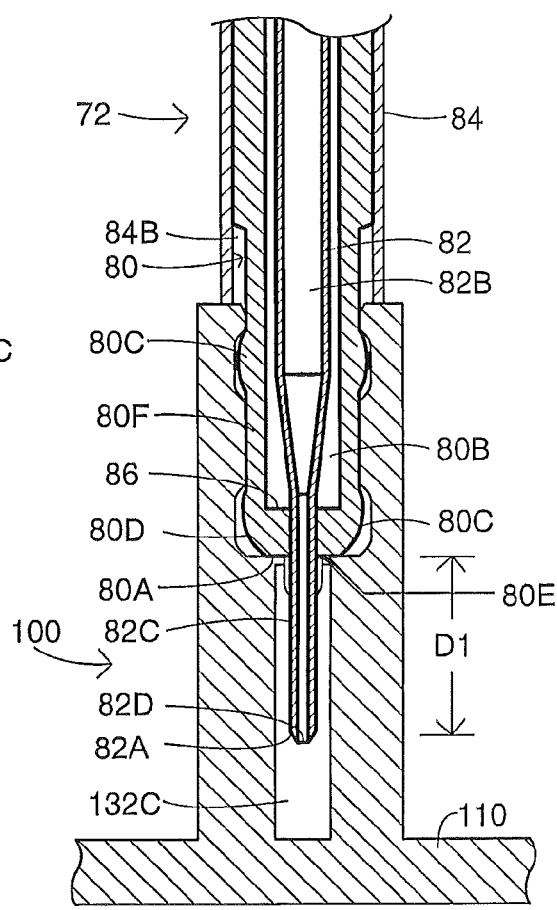
FIG. 7 is a fragmentary, cross-sectional view of the pipettor and lab member of FIG. 6 taken along the line 7-7 of FIG. 5.

A cross-sectional view of the pipettor 72 is shown in FIG. 7 and the pipettors 74, 76, 78 may be constructed in the same manner. Each pipettor 72, 74, 76, 78 includes a pipettor shaft 80, a liquid tube 82, an ejector sleeve 84, and an end wall 86. According to some embodiments, the pipettor shaft 80 is formed of metal.

Referring to FIG. 7, the pipettor shaft 80 defines a passage 80B therethrough that terminates at an opening 80E in a lower terminal end 80A of the pipettor shaft 80. A lower section 80F of the shaft 80 extends beyond the ejector sleeve 84. A pair of axially spaced apart, integral annular ribs 80C are located on the outer surface of the lower section 80F proximate the lower terminal end 80A. The lower terminal end 80A of the shaft 80 may have a generally rounded shoulder 80D. The pipettor shafts 80 of the pipettors 72, 74, 76 and 78 define pipettor axes P1-P1, P2-P2, P3-P3 and P4-P4 (FIG. 3), respectively.

The liquid tube 82 (FIG. 7) extends through the passage 80B such that a probe or tip section 82C thereof extends beyond the lower terminal end 80A a distance D1 to a lower terminal end 82A. The distance D1 can vary and, according to some embodiments, is in the range of from about 0 to 0.63 inch. A passage 82B extends through the liquid tube 82 to provide fluid communication between an end opening 82D and the liquid handler 40 (via the tubing 42). A liquid tight seal can be provided between the liquid tube 82 and the pipettor shaft 80 by the end wall 86.

The ejector sleeve 84 defines a passage 84B and surrounds the pipettor shaft 80. The ejector sleeve 84 is slidable up and down the pipettor shaft 80 under the power of the motor 58 (i.e., along the Z axis).

The actuator assemblies 72A, 74A, 76A and 78A can extend and retract (i.e., lower and raise) the pipettors 72, 74, 76 and 78, respectively, along the Z axis relative to the housing 64 and independently of one another. Additionally, each actuator assembly 72A-78A can slidably extend and retract the ejector sleeve 84 of its associated pipettor 72-78 down and up the length of the pipettor shaft 80 on which the ejector sleeve 84 is mounted.

With reference to FIGS. 2, 3, 6 and 7, the lab member 100 includes a lab object in the form of a lid structure 110 having an upper surface or side 110A. The lab member 100 further includes an adapter array 120 including a pair of primary or mounting adapter structures 122, 128 and a pair of secondary adapter structures 124, 126 integral with or coupled to the lid structure 110. According to some embodiments, the adapter structures 122, 124, 126, 128 are permanently affixed to the lid structure 110. According to some embodiments, the lab member 100 is monolithic.

The lab member 100 may be formed of any durable material or materials. According to some embodiments, the lab member 100 is formed from a material or materials that are chemically resistant, durable, and can be autoclaved without substantial loss of requisite operational properties (e.g., resilience). According to some embodiments, at least the primary adapter structures 122, 128 are formed of a resilient material and, according to some embodiments, a resilient metal or polymeric material. According to some embodiments, the adapter structures 122, 128 are formed of a material selected from the group consisting of Delrin™ acetal resin, polypropylene, polycarbonate, PTFE (Teflon™), aluminum and stainless steel. According to some embodiments, the material of the adapter structures 122, 128 has a Young's Modulus in the range of from about 0.5 GPa to 200 GPa. According to some embodiments, at least the primary adapter structures 122, 128 are molded. According to some embodiments, the adapter structures 122, 124, 126, 128 and the lid structure 110 are unitarily molded. According to other embodiments, the adapter structures 122, 124, 126, 128 are separately formed from the lid structure 110 and affixed to the lid structure such as by adhesive, welding or fasteners.

Figure 2:
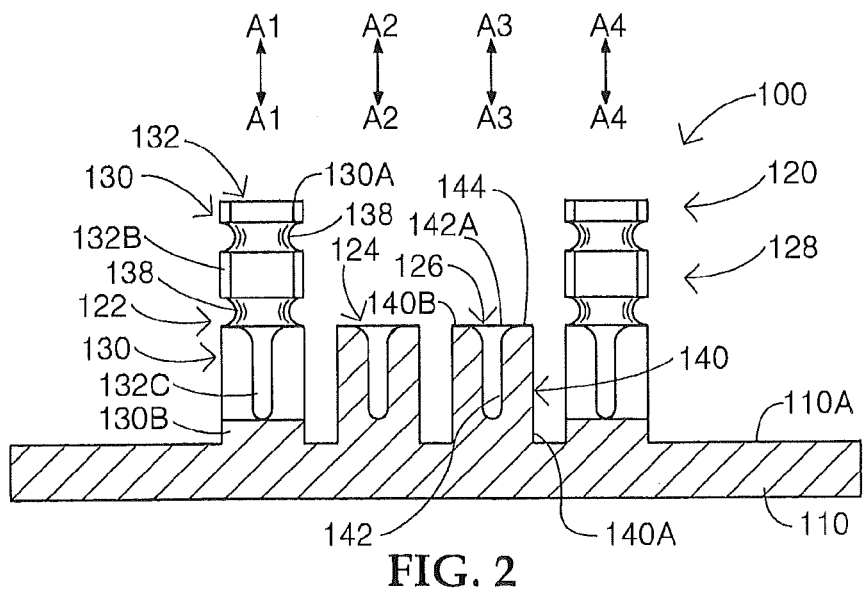
FIG. 2 is a cross-sectional view of the lab member of FIG. 1 taken along the line 2-2 of FIG. 3.
Figure 6:
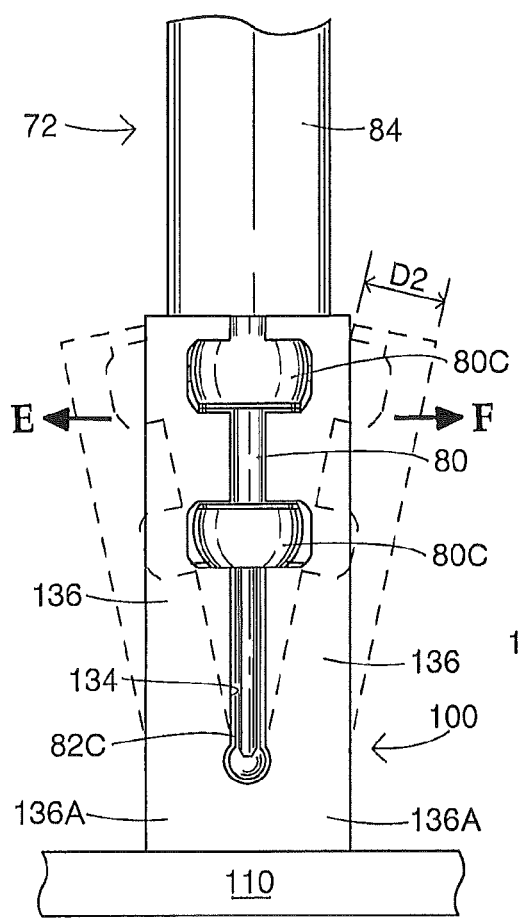
FIG. 6 is a fragmentary, side view of a pipettor of the pipetting module of FIG. 1 engaged with a primary adapter structure of the lab member.

Each primary adapter structure 122, 128 includes a tubular body 130 having an upper end 130A and a lower end 130B. The lower end 130B is joined to or merged with the upper surface 110A of the lid structure 110. The body 130 defines a passage or socket 132 and a top opening 132A communicating with the socket 132. The socket 132 has an enlarged section 132B and a reduced section 132C. The socket 132 of the adapter structure 122 defines an adapter axis A1-A1 and the socket 132 of the adapter structure 128 defines an adapter axis A4-A4 (FIG. 2). Opposed axially extending side expansion slots 134 are defined in the body 130 to form opposed arms 136 (FIG. 6). The arms 136 can be elastically deflected apart (in opposed directions E and F) about their bases 136A. A pair of axially spaced apart annular grooves 138 (FIG. 2) are defined in the enlarged section 132B. Each annular groove 138 is bisected by the expansion slots 134.

With reference to FIG. 2, each secondary adapter structure 124, 126 includes a body 140 having opposed upper and lower ends 140A, 140B. The lower end 140B is joined to or merged with the lid structure 110. A passage or socket 142 extends through the body 140 from a top opening 142A. An abutment shoulder 144 is provided on the upper end 140A. The socket 142 of the adapter structure 124 defines an adapter axis A2-A2 and the socket 142 of the adapter structure 126 defines an adapter axis A3-A3.

Exemplary operation of the system 10 and use of the lab member 100 in accordance with methods of the present invention will now be described with reference to FIGS. 1 and 3-9. Initially, the lab member 100 may be seated in the holder 14 and the container 18 may be seated in the holder 16 on the deck 12. The container 18 may include one or more liquid samples and be open. When it is desired to cover the container 18, the pipetting module 60 and the adapter array 120 can be used as follows to install the lab member 100 on the container 18. According to some embodiments, the following procedure is executed via or by the controller 30, which controls actuation of the drive motors 54, 56, 58.

The pipetting module 60 is repositioned on the frame 20 and with respect to the deck as needed to align the pipettor axes P1-P1, P2-P2, P3-P3 and P4-P4 with the adapter axes A1-A1, A2-A2, A3-A3 and A4-A4, respectively, as shown in FIGS. 1 and 3. If needed, the controller 30 may adjust the height of the pipetting module 60 (e.g., lower the pipetting module 60). The controller 30 then drives the pipettors 74 and 76 down (i.e., in the direction—Z) along the axes P2-P2 and P3-P3 such that the pipettor shafts 80 thereof are inserted into the sockets 142 of the secondary adapter structures 124 and 126, respectively. The tip 82C of each pipettor 74, 76 is received in the socket 142 of the corresponding adapter structure 124, 126 and each pipettor 74, 76 abuts the shoulder 144 of the corresponding adapter structure 124, 126. The lab member 100 is thereby secured in place by the pipettors 74, 76.

Figure 5:
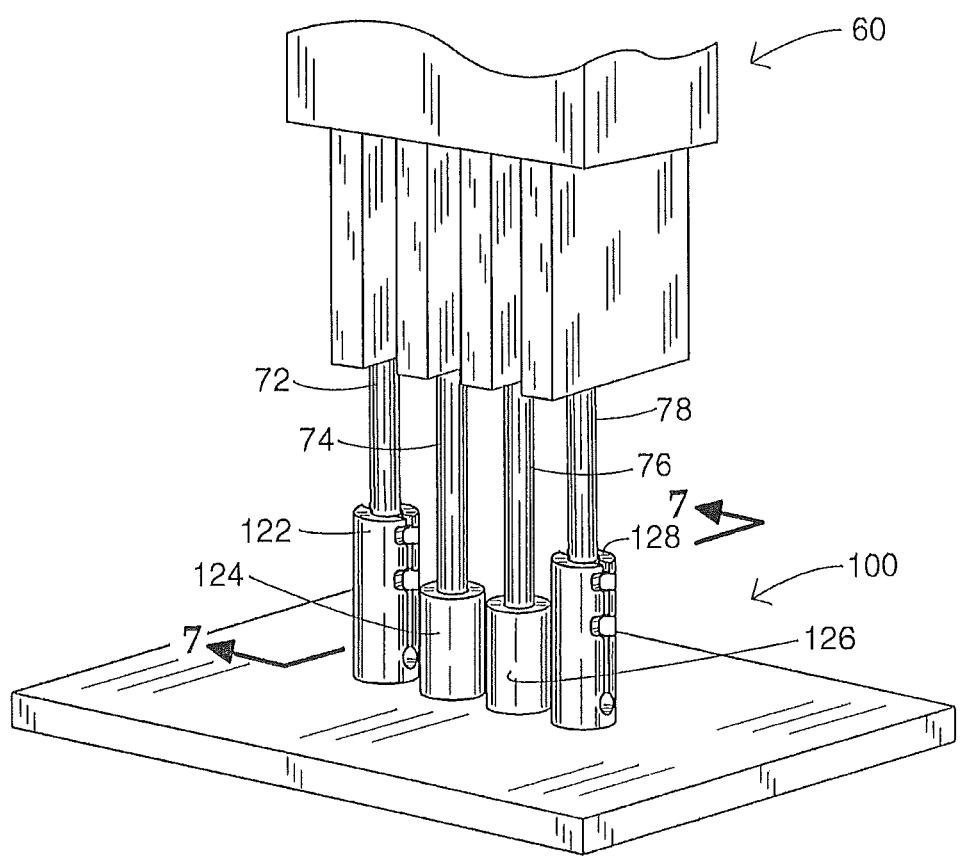

Next, the controller 30 drives the pipettors 72 and 78 down along the axes P1-P1 and P4-P4 such that the shafts 80 thereof are inserted into the sockets 132 of the primary adapter structures 122 and 128, respectively, as shown in FIGS. 5-7. The tip 82C of each pipettor 72, 78 is received in the socket section 132C and the lower section 80F of each pipettor 72, 78 is received in the socket section 132B of the corresponding adapter structure 122, 128. As each lower section 80F is inserted into its socket 132, the ribs 80C thereof urge or force the arms 136 to deflect radially outwardly about their ends 136A to an open or receiving position as indicated in dashed lines in FIG. 6. According to some embodiments, the maximum deflection distance D2 (FIG. 6) is in the range of from about 0.35 to 0.75 mm. Once the shaft 80 is fully inserted, the annular grooves 138 permit the arms 136 to elastically return to their closed or clamping position as shown in solid lines in FIGS. 6 and 7. The annular ribs 80C are thereby captured in the annular grooves 138 and the adapter structure 122 or 128 generally snugly conforms to the lower section 80F. The ribs 80C and the grooves 138 serve as interlock structures that cooperate to mechanically interlock the shaft 80 with the primary adapter structure 122 or 128 and thereby prevent or inhibit relative axial displacement between the shaft 80 and the lab member 100.

Figure 8:
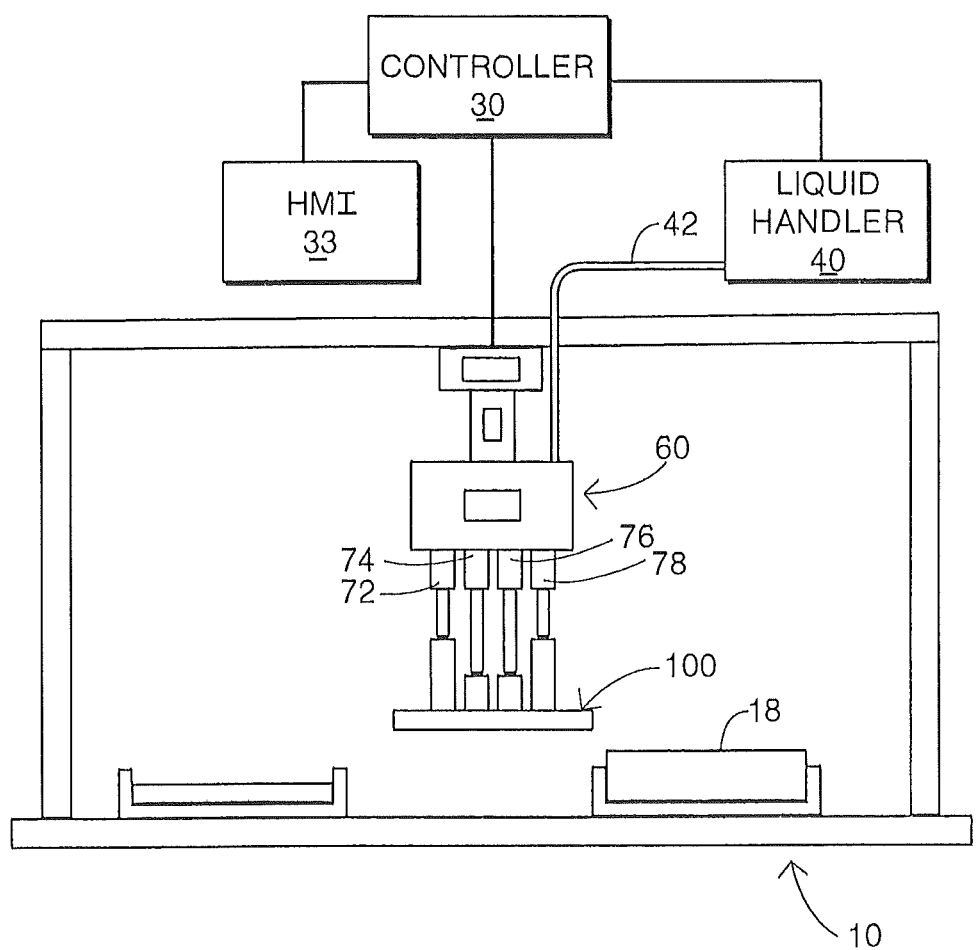
FIGS. 8 and 9 are schematic diagrams of the laboratory liquid handling system of FIG. 1 illustrating the pipetting module transporting and depositing the lab member.
Figure 9:
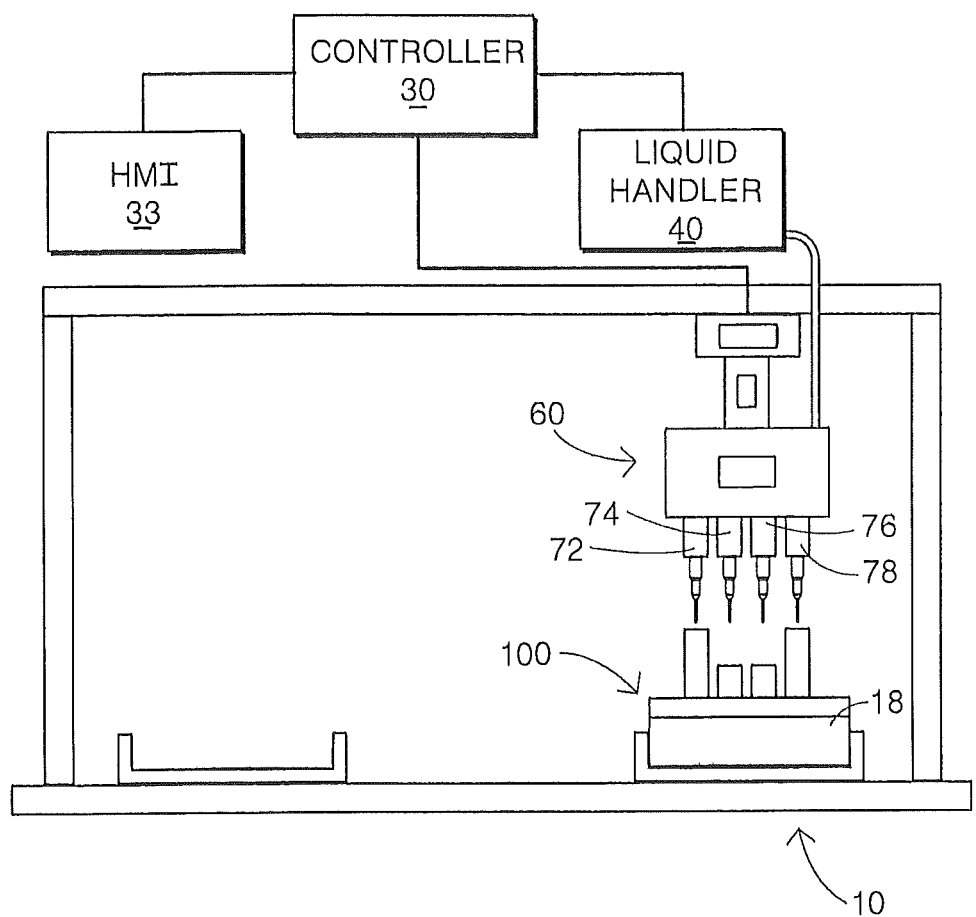

With the lab member 100 secured to or mounted on the pipetting module 60 as described, the lab member 100 can be lifted, transported across the deck 12, and placed on the container 18 as illustrated in FIGS. 8 and 9, or another desired location.

Once the lab member 100 has been placed in the desired location, the lab member 100 can be released or disengaged as follows. The controller 30 retracts the shafts 80 of the pipettors 72 and 78 from the primary adapter structures 122 and 128 while the shafts 80 of the pipettors 74 and 76 (which are still seated in the secondary adapter structures 124 and 126) hold the lab member 100 in place. The arms 136 of the adapter structures 122, 128 deflect radially outwardly to release the lower sections 80F. Thereafter, the controller 30 retracts the shafts 80 of the pipettors 74 and 76 from the adapter structures 124, 126.

According to some embodiments, the controller 30 maintains the ejector sleeves 84 of the pipettors 72, 78 in place adjacent or in abutment with the upper ends 130A of the adapter structures 122, 128 while the shafts 80 of the pipettors 72, 78 are retracted in order to assist in stabilizing the lab member 100 during disengagement.

According to some embodiments and as illustrated, the pipettors 74, 76 fit loosely in the sockets 142 of the adapter structures 124, 126 so that the pipettors 74, 76 can be inserted into and withdrawn from the sockets 142 without undesirably displacing the lab member 100.

According to some embodiments, the adapter structures 122, 124, 126, 128 do not form an airtight seal about the corresponding pipettors 72, 74, 76, 78.

The procedure as described above can be repeated for replacement of the lab member 100 and/or transport and placement of other members provided with adapter structures as described.

The pipettors 72, 74, 76, 78 can continue to be used for pipetting using the tips 82C thereof when the pipettors 72, 74, 76, 78 are not installed in the adapter structures. Thus, the liquid handling system 10 can otherwise function in known or other desired manner. For example, the controller 30 can place one or more of the tips 82C of the pipettors 72, 74, 76, 78 in or over a volume of a liquid sample (e.g., in a cell or cells of a microwell plate or other container on the deck 12) and the liquid handler 40 can then aspirate and collect liquid from the volume or dispense a material into the volume. If liquid is collected, the controller 30 can thereafter move the pipettor(s) 72, 74, 76, 78 in or over another location (e.g., cells or containers different from those from which the liquid was collected) and dispense the liquid onto or into this new location.

Figure 10:
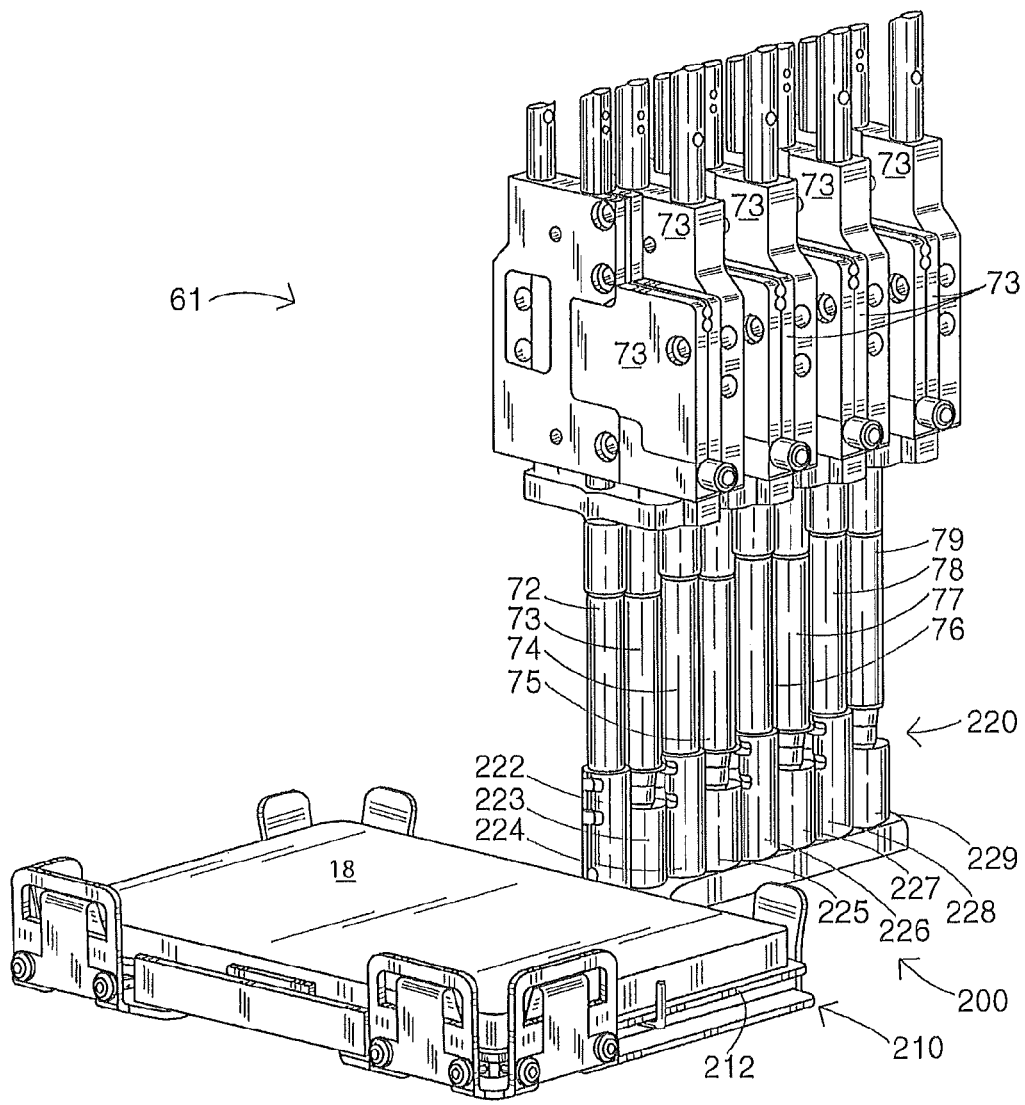
FIG. 10 is a fragmentary, perspective view of a laboratory liquid handling system according to further embodiments of the present invention.

With reference to FIG. 10, a lab member 200 according to further embodiments of the present invention is shown therein with a pipetting module 61. The pipetting module 61 can be incorporated in the system 10 and used in the same manner as the pipetting module 60. The pipetting module 61 can be configured in the same manner as the pipetting module 60 except that the pipetting module 61 includes eight pipettors 72, 73, 74, 75, 76, 77, 78 and 79, each coupled to a housing (not shown) by a respective actuator assembly 73.

The lab member 200 includes a lab object in the form of a carrier 210, and an integral adapter array 220. The carrier 210 includes a tray or platter 212 and an extension or handle 214. The platter 212 may be configured to hold a receptacle or container 18 (e.g., a microwell plate), for example.

The adapter array 220 includes four primary adapter structures 222, 224, 226, 228 alternating in series with four secondary adapter structures 223, 225, 227, 229. The primary adapter structures 222, 224, 226, 228 correspond to and can be constructed and configured in the same manner as the primary adapter structures 122, 128. The secondary adapter structures 223, 225, 227, 229 correspond to and can be constructed and configured in the same manner as the secondary adapter structures 124, 126.

The pipetting module 61 and the lab member 200 can be used in generally the same manner as the pipetting module 60 and the lab member 100 to transport objects (e.g., the container 18). More particularly, the pipettors 73, 75, 77 and 79 can be engaged with secondary adapter structures 223, 225, 227 and 229 to locate, brace, and stabilize the carrier 210 and the primary adapter structures 72, 74, 76 and 78 can be engaged and interlocked with the primary adapter structures 222, 224, 226 and 228 to secure the pipetting module 61 to the lab member 200.

Figure 11:
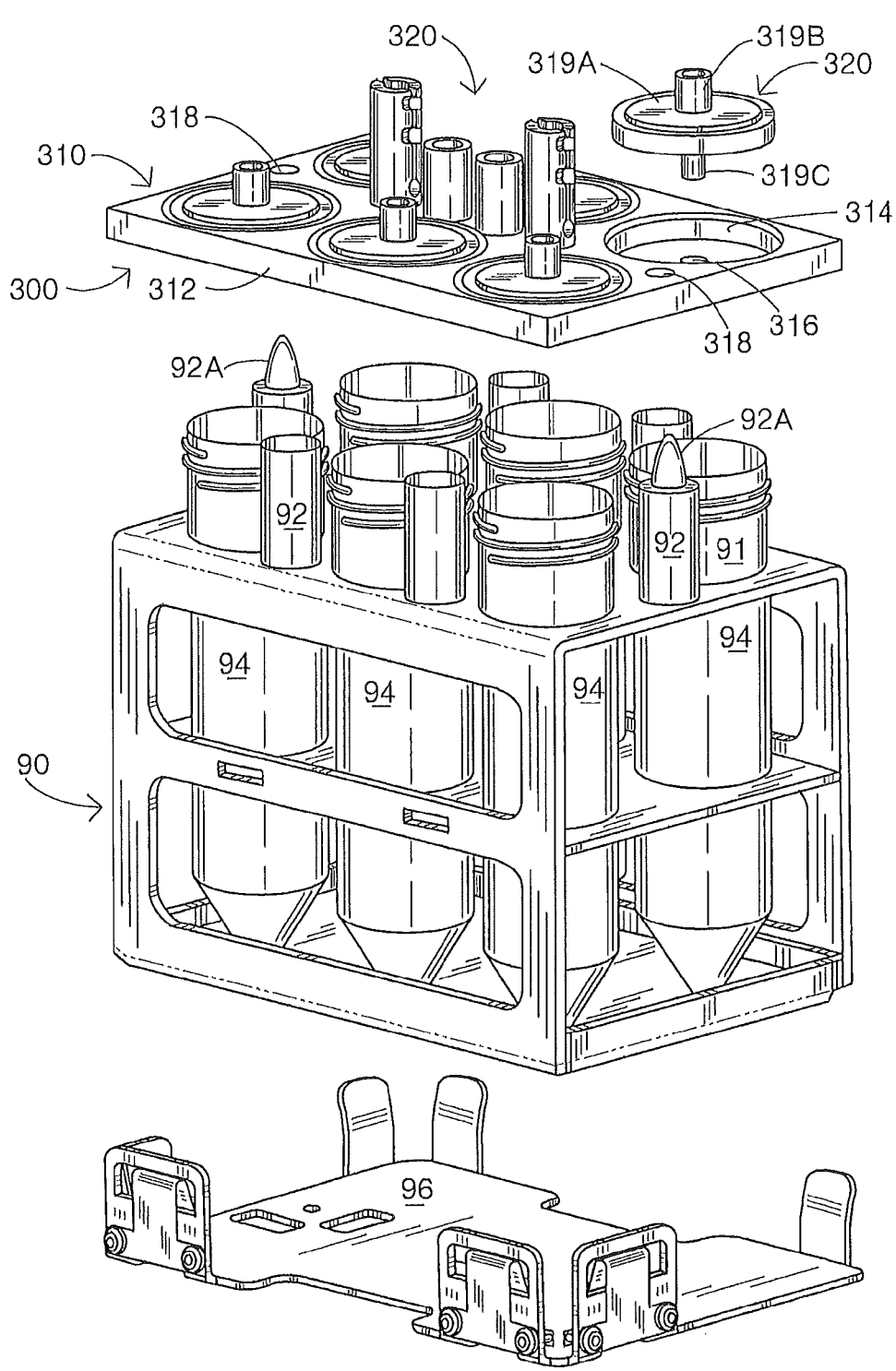
FIG. 11 is an exploded, fragmentary, perspective view of a laboratory liquid handling system according to further embodiments of the present invention.

With reference to FIG. 11, a lab member 300 according to further embodiments of the present invention is shown therein with a rack 90, a plurality of sample vials 94, and a rack holder 96 to hold the rack 90. The lab member 300 and the rack 90 can be incorporated into the liquid handling system 10 as described above, for example.

The rack 90 defines slots 91 to hold the vials 94 in place. Spacers 92 project upwardly from the rack 90. Opposed ones of the spacers 92 include alignment posts 92A.

The lab member 300 includes a lab object in the form of a filter disk assembly 310, and an integral adapter array 320. The filter disk assembly 310 includes a carrier body 312. Filter seats 314, filter holes 316 and alignment holes 318 are defined in the carrier body 312. Filters 320 are mounted in each of the filter seats 314. The filters 320 may be of any suitable type or construction. The filters 320 may include, for example, a filter housing 319A containing filter media and having an inlet nozzle 319B and an outlet nozzle 319C. The outlet nozzles 319B are received in the filter holes 316 to direct filtered fluid into the vials 94.

The adapter array 320 can be constructed and configured as described above with regard to the adapter array 120. The pipetting module 60 and the adapter array 320 can thus be used in the same manner as described above to transport the filter disk assembly 310 to and/or from the rack 90 and to mount the filter disk assembly 310 on and/or remove the filter disk assembly 310 from the rack 90. When the lab member 300 is placed on the rack (and, more particularly, on the spacers 92) the alignment posts 92A are received in the alignment holes 318 to positively align the filters 319 with the vials 94.

Figure 12:
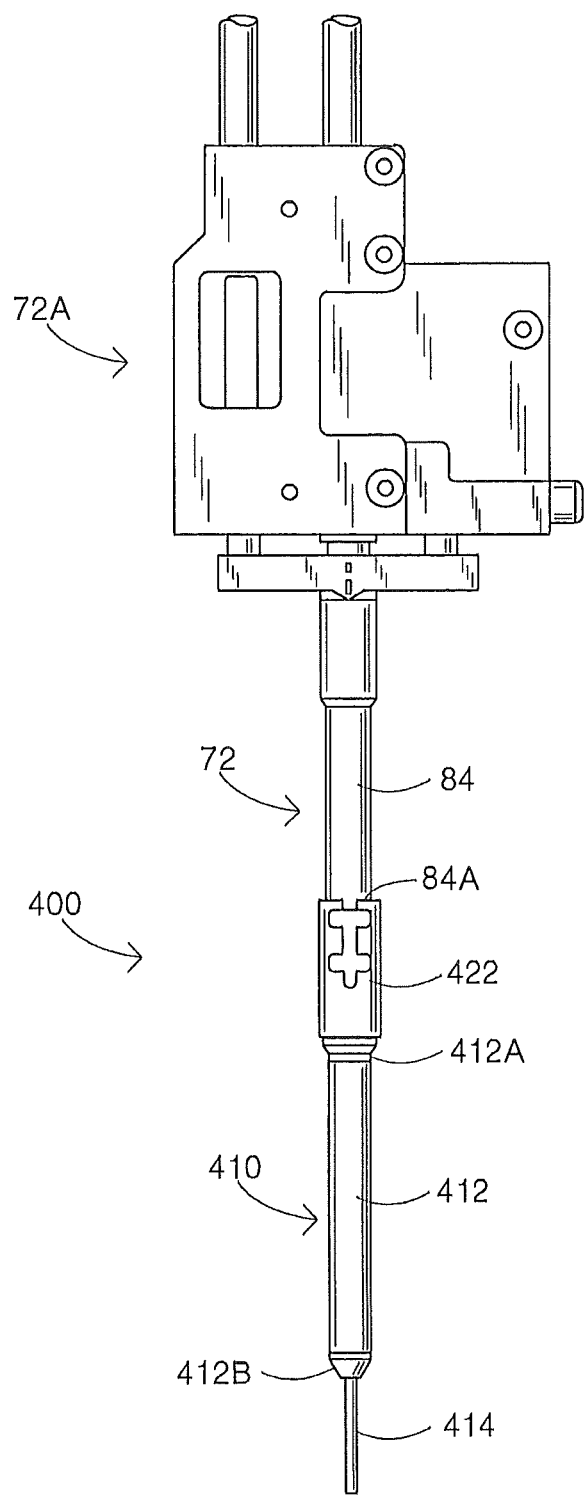
FIG. 12 is an exploded, fragmentary, side view of a laboratory liquid handling system according to further embodiments of the present invention.

With reference to FIG. 12, a lab member 400 according to further embodiments of the invention is shown therein mounted on the pipettor 72. For the purpose of illustration, the remainder of the pipetting module 60, other than the actuator assembly 72A, is not shown in FIG. 12.

The lab member 400 includes a lab tool in the form of a pin tool 410, and an integral adapter structure 422. The pin tool 410 includes a tip 414 and a body or shaft 412 having opposed ends 412A, 412B. The adapter structure 422 is mounted on the end 412A and the tip 414 extends from the end 412B. The lab member 400 may be monolithic or integrally formed (e.g., integrally molded).

The adapter structure 422 corresponds to the adapter structure 122 and may be constructed and configured in the same manner as described above.

The lab member 400 can be used as follows. The lab member 400 may be initially positioned in a holder that holds the lab member 400 upright. The controller 30 drives the pipettor shaft 80 of the pipettor 72 into the socket 432 of the adapter structure 422 to releasably secure the lab member 400 to the pipettor 72. The controller 30 can direct the pipetting module 60 to move the lab member 400 above a sample (e.g., a liquid sample in a container such as a microwell plate), extend the pipettor 72 downwardly to dip the tip 414 into the sample, and retract the pipettor 72 to withdraw the tip 414 (with a droplet from the liquid sample collected thereon) from the liquid sample. The pipetting module 60 can then transport the lab member 400 (with the droplet held on the tip 414) to a desired location and deposit the droplet, which can be released from the tip 414 by touching the droplet to a target surface. If desired, the foregoing droplet transfer procedure may be executed multiple times. The tip 414 may be cleaned by dipping in a wash fluid, for example, between droplet collections.

When it is desired to remove the lab member 400 from the pipettor 72, the controller 30 slidably extends or drives the ejector sleeve 84 down the length of the shaft 80. The lower end 84A of the ejector sleeve 84 abuts the top end of the adapter structure 422 and pushes the adapter structure 422, and thereby the lab member 400, axially off of the pipettor 72.

Figure 13:
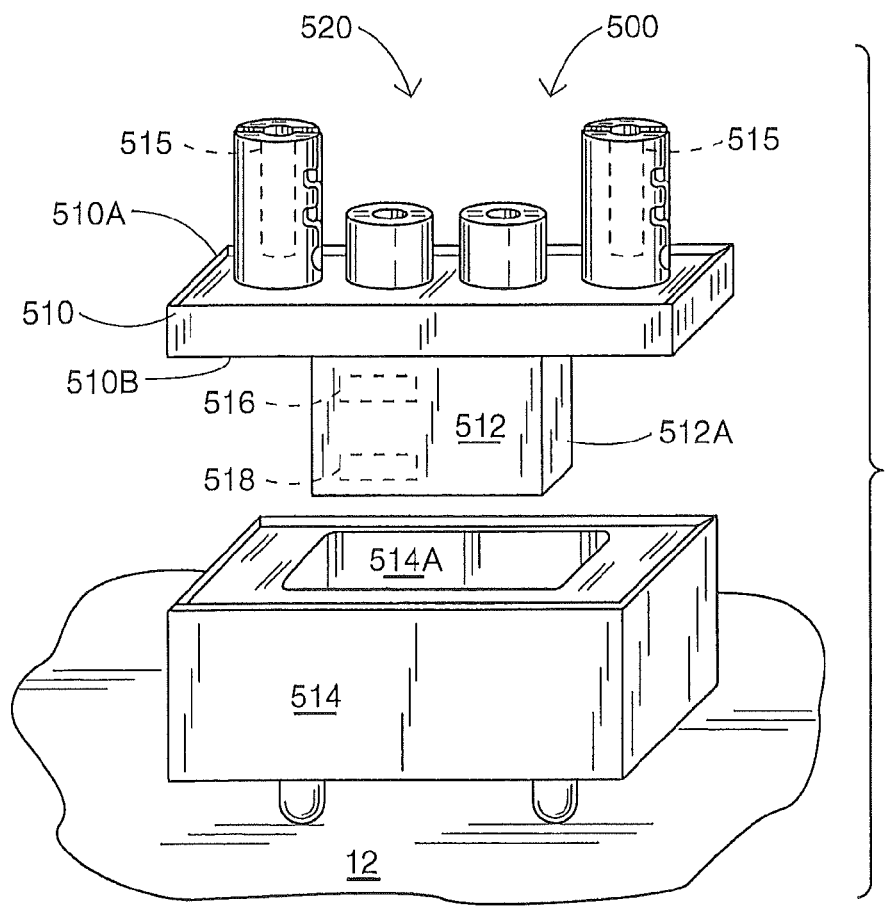
FIG. 13 is an exploded, fragmentary, perspective view of a laboratory liquid handling system according to further embodiments of the present invention.
Figure 14:
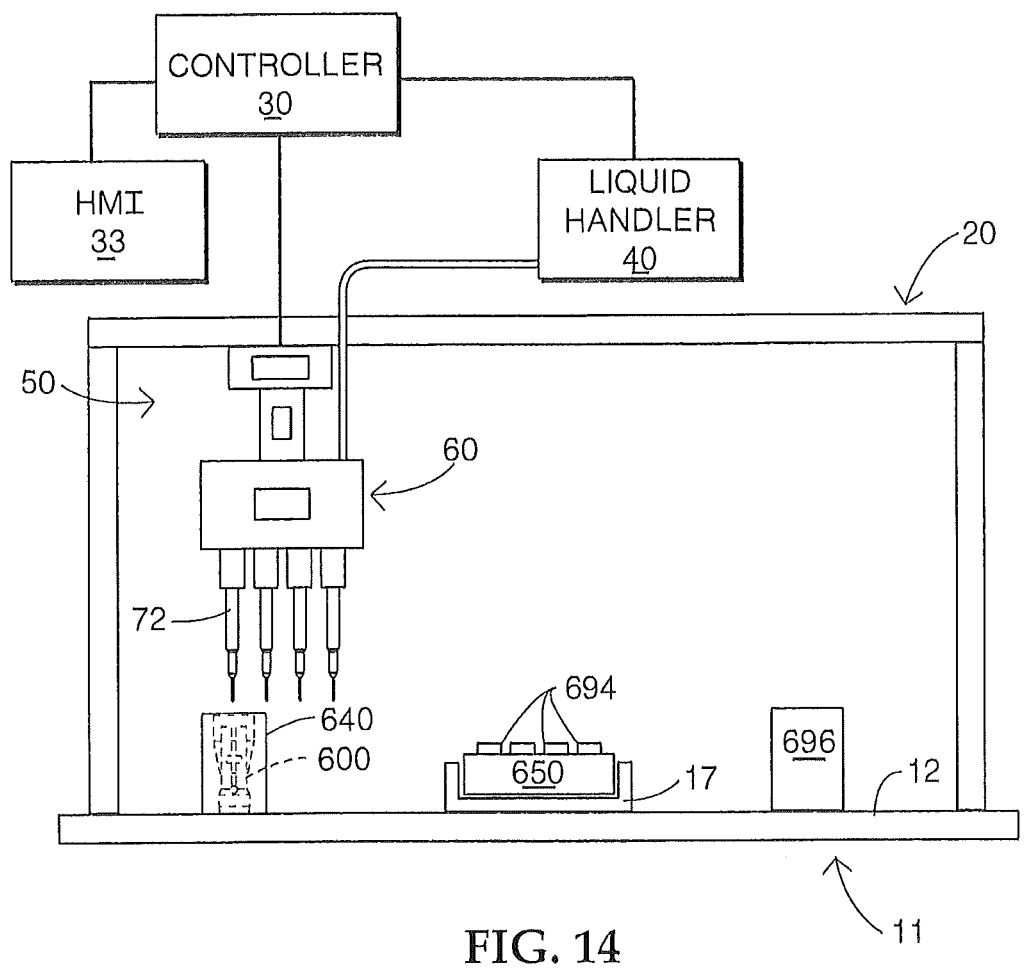
FIG. 14 is a schematic diagram of a laboratory liquid handling system according to further embodiments of the present invention and including a pipetting module and a lab member and a container rack according to further embodiments of the present invention.

With reference to FIG. 13, a lab member 500 according to further embodiments of the present invention is shown therein. The lab member 500 can be used in conjunction with a holder 515 and the pipetting module 60 (not shown in FIG. 13).

The lab member 500 includes a body or base 510, an integral adapter array 520 on an upper side 510A of the base 510, and an integral sensor module 512 mounted on an opposing lower side 510B of the base 510. The adapter array 520 can be constructed and configured as described above with regard to the adapter array 120. The pipetting module 60 and the adapter array 520 can be used in the same manner as described above to transport the sensor module 512 to and from desired locations. For example, the lab member 500 can be initially mounted in the holder 514 with the sensor module 512 seated in a slot 514A. The controller 30 can operate the pipetting module 60 to engage the adapter array 520, withdraw the lab member 500 from the holder, position the sensor module 512 in a desired location (e.g., adjacent or on a sample, transponder, label, or the like), return the lab member 500 to the holder 514, and eject the lab member 500 from the pipettors 72, 74, 76, 78.

According to some embodiments, the sensor module 512 includes a housing 512A holding a transducer 518 or other sensing device. The sensor module 512 may further include an onboard controller 516.

The sensor module 512 may include any suitable type of sensor or sensors such as an ultrasonic sensor, an optical sensor, or a temperature sensor.

With reference to FIGS. 14-24, a liquid handling system 11 according to further embodiments of the present invention is shown therein. In FIGS. 14-24 and the description that follows, like reference numerals refer to the corresponding components as referred to above with regard to the system 10.

The system 11 includes the deck 12, the frame 20, the controller 30, the liquid handler 40, the drive system 50 and the pipetting module 60, each of which can be operated generally in the manner described hereinabove. The system 11 further includes a lab member 600 according to embodiments of the invention, a tool holder 640, a rack holder 17, a container rack 650 and one or more sample vials 694.

Figures 15, 16:
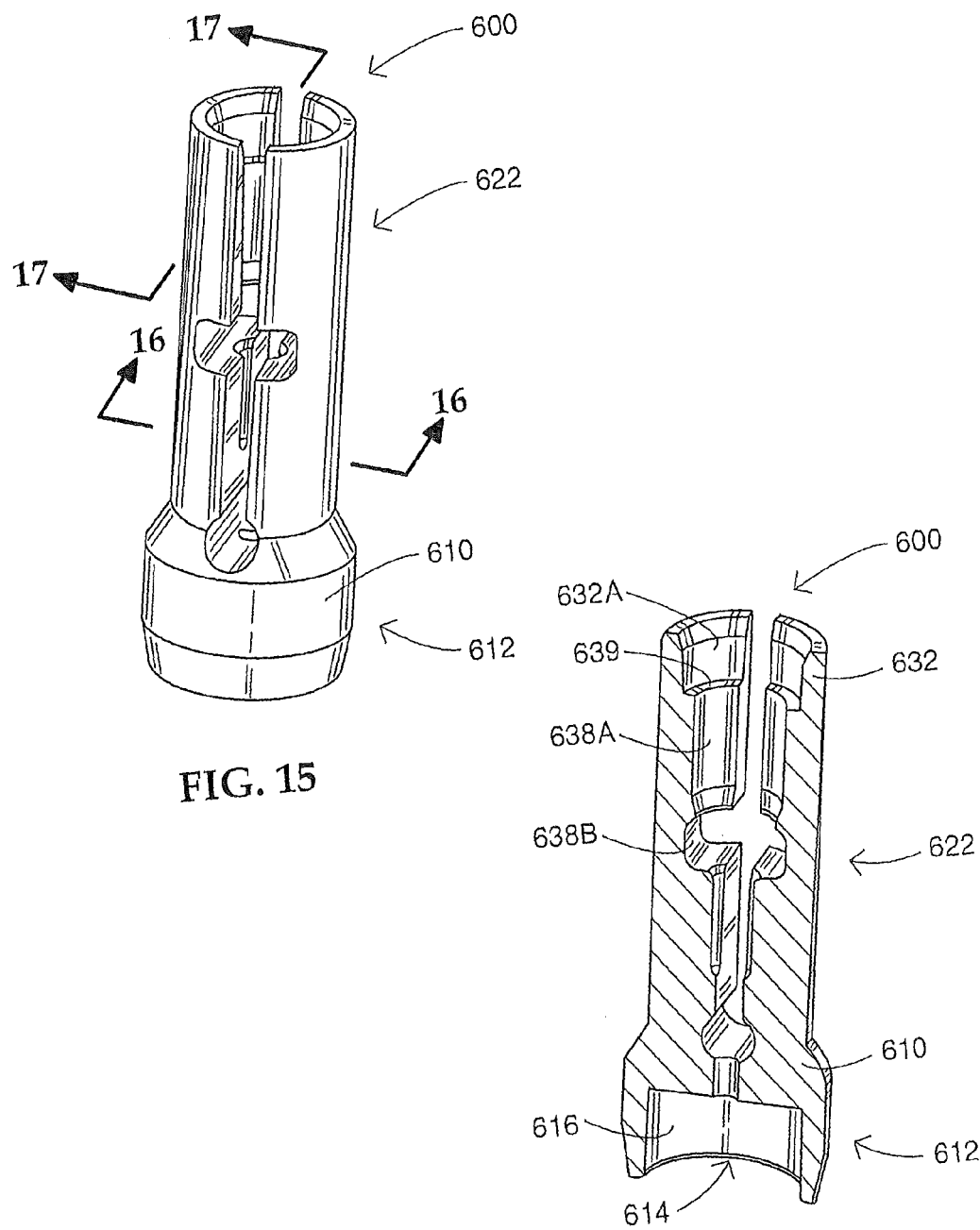
FIG. 15 is a top, perspective view of the lab member of FIG. 14.
FIG. 16 is a cross-sectional, perspective view of the lab member of FIG. 14 taken along the line 16-16 of FIG. 15.
Figures 17, 18:
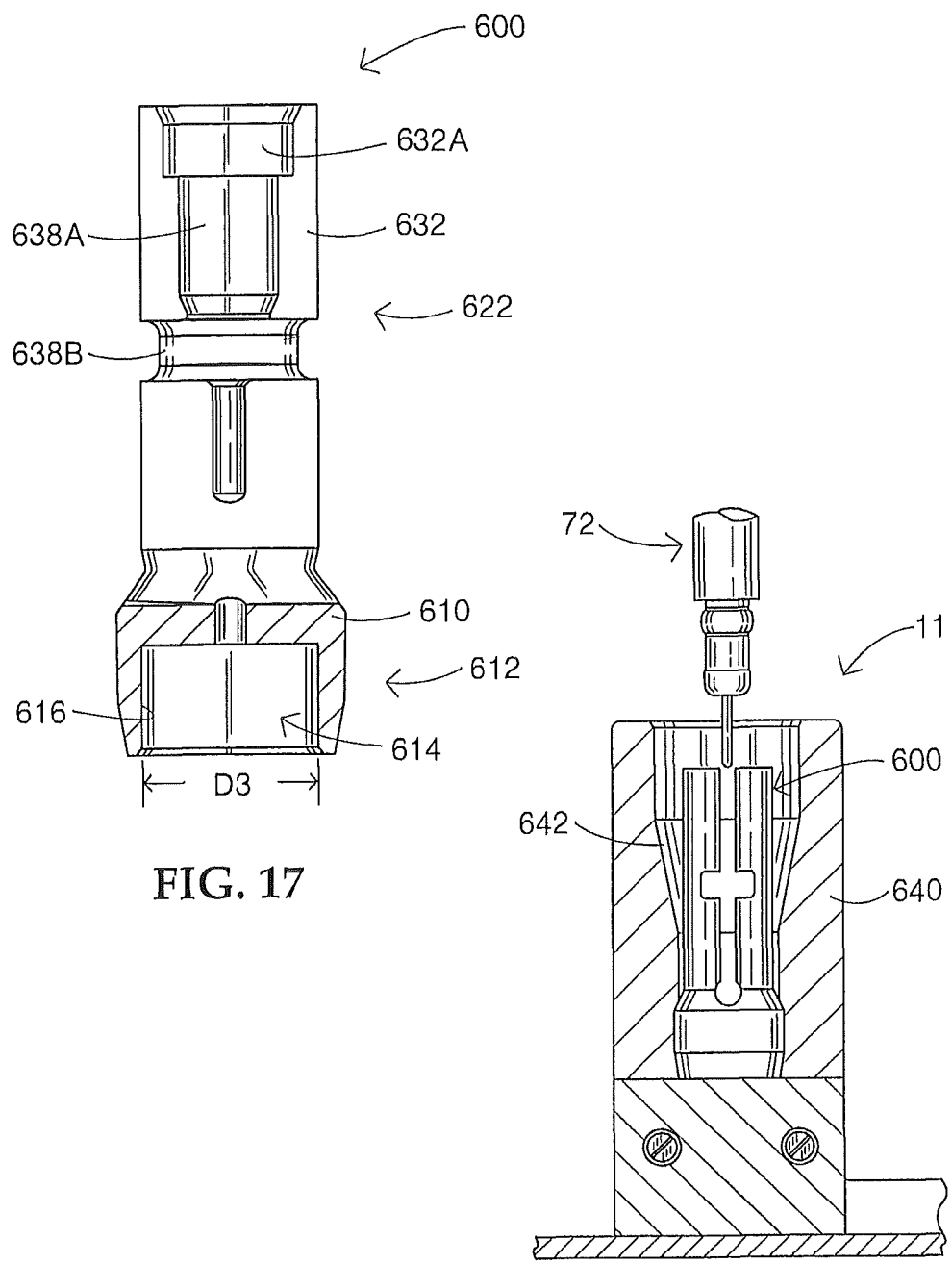
FIG. 17 is a cross-sectional view of the lab member of FIG. 14 taken along the line 17-17 of FIG. 15.
FIGS. 18 and 19 are fragmentary, cross-sectional views of the laboratory liquid handling system of FIG. 14 illustrating a sequence of steps to mount the lab member of FIG. 14 on the pipetting module.

With reference to FIGS. 15-17, the lab member 600 includes a body 610, an integral adapter structure 622 on an upper end of the body 610, and an integral head 612 on an opposing lower end of the body 610. The lab member 600 may be monolithic or integrally formed (e.g., integrally molded).

The adapter structure 622 is generally constructed and configured in the same manner as the adapter structure 122, except as follows. The upper annular groove 638A is axially elongated so that, when the pipettor shaft 80 is inserted, the lower rib 80C interlocks with the lower annular groove 638B but the upper rib 80C does not interlock with the upper groove 638A. Additionally, the upper end of the adapter structure 622 is provided with an upper flange 632 defining a socket 632A that can receive the lower end of the ejector sleeve 84. The adapter structure 622 may include a shoulder 639 that abuts or limits insertion of the ejector sleeve 84.

The head 612 defines a downwardly opening socket 614 having a circumferential inner side wall surface 616.

Figure 21:
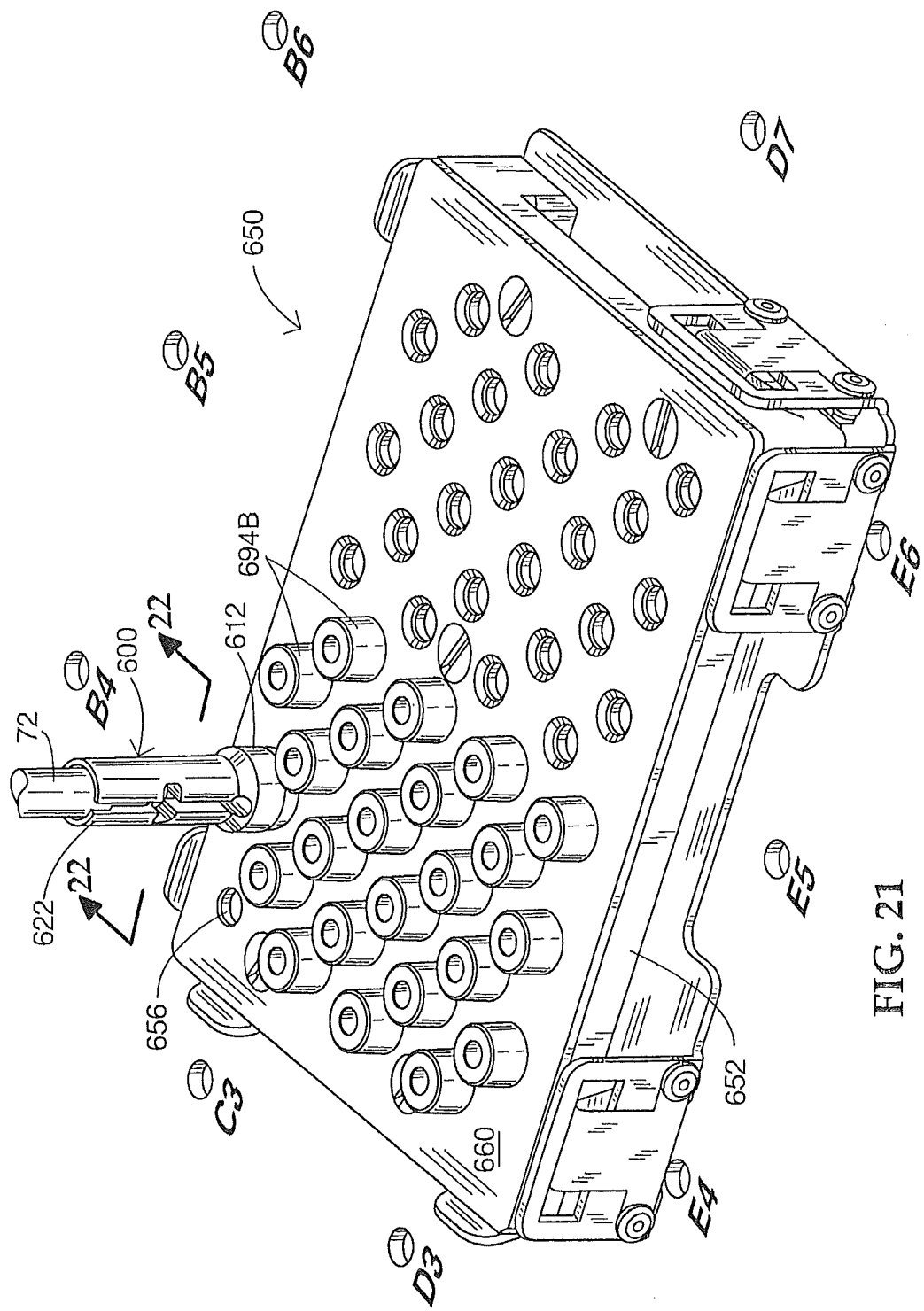
FIG. 21 is a perspective view of the pipetting module and the lab member of FIG. 14 engaging the vial in the container rack.
Figure 22:
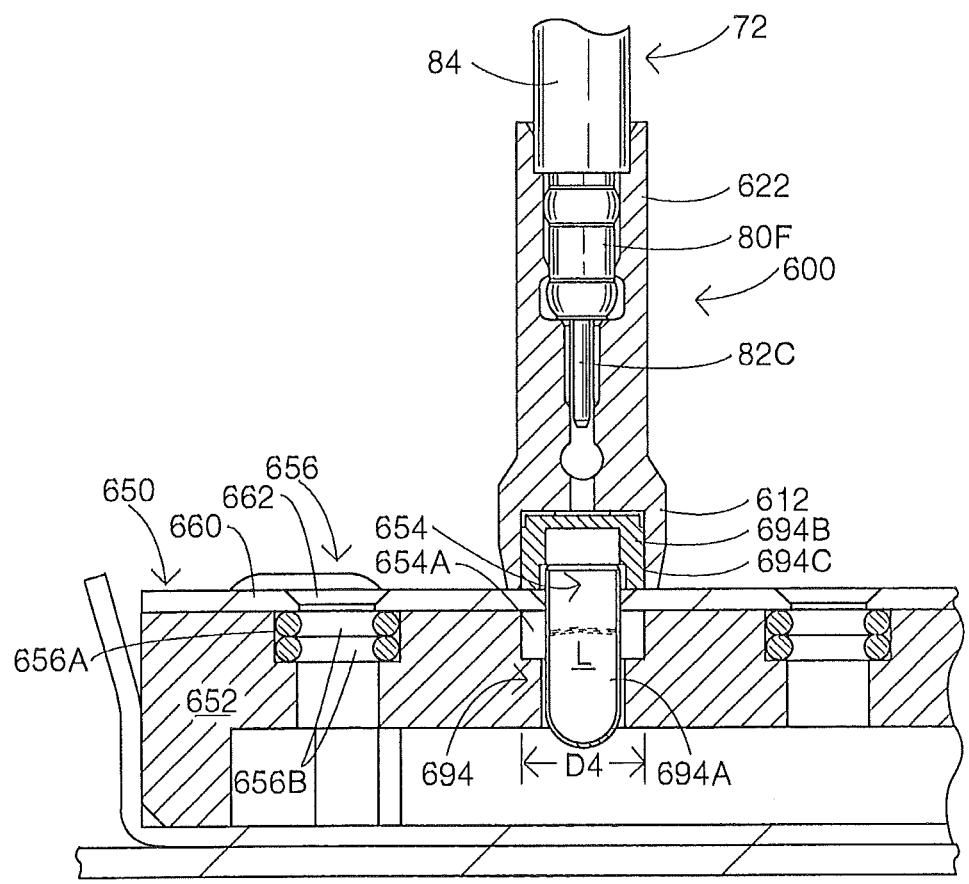
FIG. 22 is a cross-sectional view of the pipetting module, the lab member, the vial and the container rack taken along the line 22-22 of FIG. 21.

With reference to FIGS. 21 and 22, the container rack 650 includes a base 652 and a cover 660. The base 652 includes an array of container slots 654, 656. The container slots 654, 656 each have upper enlarged sections 654A, 656A. Gripping elements 656B, such as elastomeric O-rings, are seated in the enlarged sections 656A. A cover 660 overlies the base 652 and captures the gripping elements 656B in the enlarged section 656A. The cover 660 has openings 662 aligned with the slots 654, 656.

Referring to FIG. 22, each vial 694 includes a closed end tube or vessel 694A and an end cap 694B to seal the open end of the vessel 694A. The end cap 694B has a circumferential outer wall surface 694C.

Figure 19:
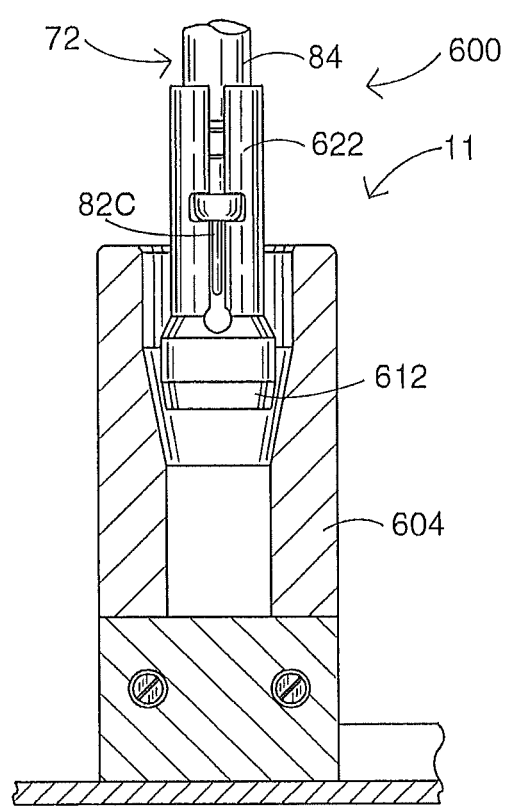

The system 11 can be used as follows in accordance with methods of the present invention. The lab member 600 may be initially stored in a slot 642 of tool holder 640 as shown in FIG. 18. The controller 30 moves the pipetting module 60 to axially align the pipettor 72 with the adapter structure 622 (FIG. 18). The controller 30 then extends the pipettor 72 to engage and interlock the lower section 80F of the pipettor shaft 80 with the adapter structure 622, and retracts the pipettor 72 to withdraw the lab member 600 from the holder 640 (FIG. 19).

Figure 20:
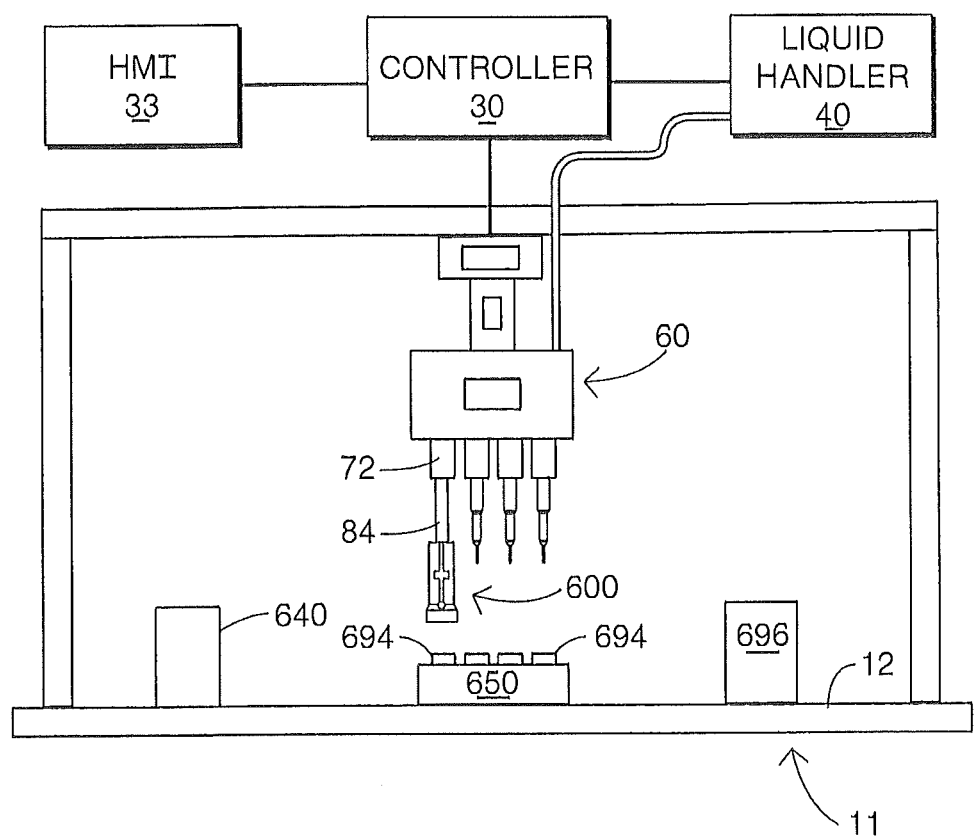
FIG. 20 is a schematic diagram of the laboratory liquid handling system of FIG. 14 illustrating the pipetting module and the lab member aligned with a vial in the container rack.

The pipetting module 60 is then moved to align the tool head 612 with the cap 694B of a selected vial 694 in the rack 650 (FIG. 20). The pipettor 72 is then extended to press the tool head 612 down onto the cap 694B such that the cap 694B is seated in the socket 614 (FIGS. 21 and 22).

The head 612 and the cap 694B are relatively sized and configured such that the head 612 exerts a gripping force on and/or interlocks with the cap 694B. According to some embodiments, an inner diameter D3 (FIG. 17) of the socket 614 is the same as or less than a mating outer diameter D4 (FIG. 22) of the cap 694B so that the head 612 grips the cap 694B with an frictional interference fit between the socket inner surface 616 and the cap outer surface 694C. In some embodiments, one or both of the surfaces 616, 694C are textured or coated with a material to enhance the friction between the surfaces 616, 694C. The head 612 may be resilient such that the cap 694B slightly radially outwardly expands the head 612, which in turn elastically applies a radially inward gripping or clamping force to the cap 694B.

The controller 30 then retracts the pipettor 72. The holding force $F_G$ between the head 612 and the cap 694B is greater than the resistance force $F_{R1}$ imparted on the vial 694 (where $F_{R1}$ includes the weight load $F_W$ of the vial 694 and its contents and any friction and/or grip force $F_{S1}$ applied to the vial 694 by the rack 650) so that the vial 694 is withdrawn from the rack 650 and the cap 694B thereof remains firmly seated in the socket 614.

Figure 23:
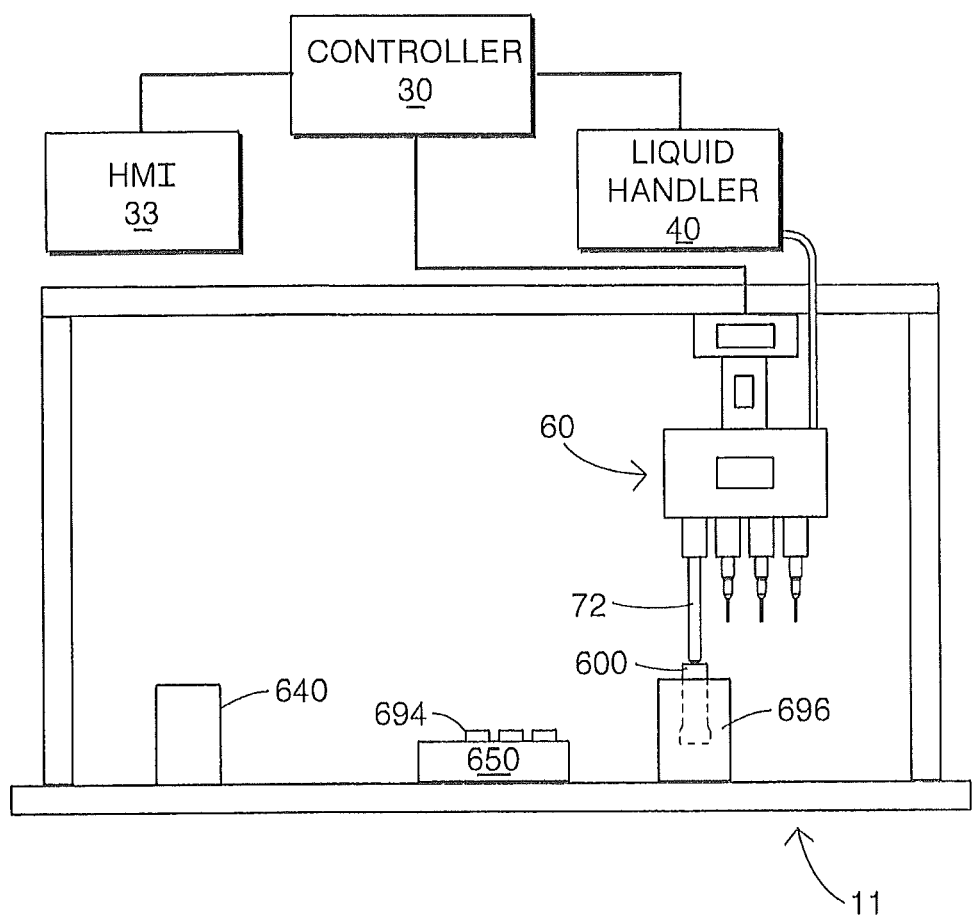
FIG. 23 is a schematic diagram of the laboratory liquid handling system of FIG. 14 illustrating the pipetting module and the lab member positioning the vial in a station.

The pipetting module 60 can then be moved about the deck 12 and the pipettor 72 can be extended to reposition the vial 694 as desired. For example, the vial 694 can be inserted into and held in an analyzer or sensor apparatus 696 as shown in FIG. 23.

Figure 24:
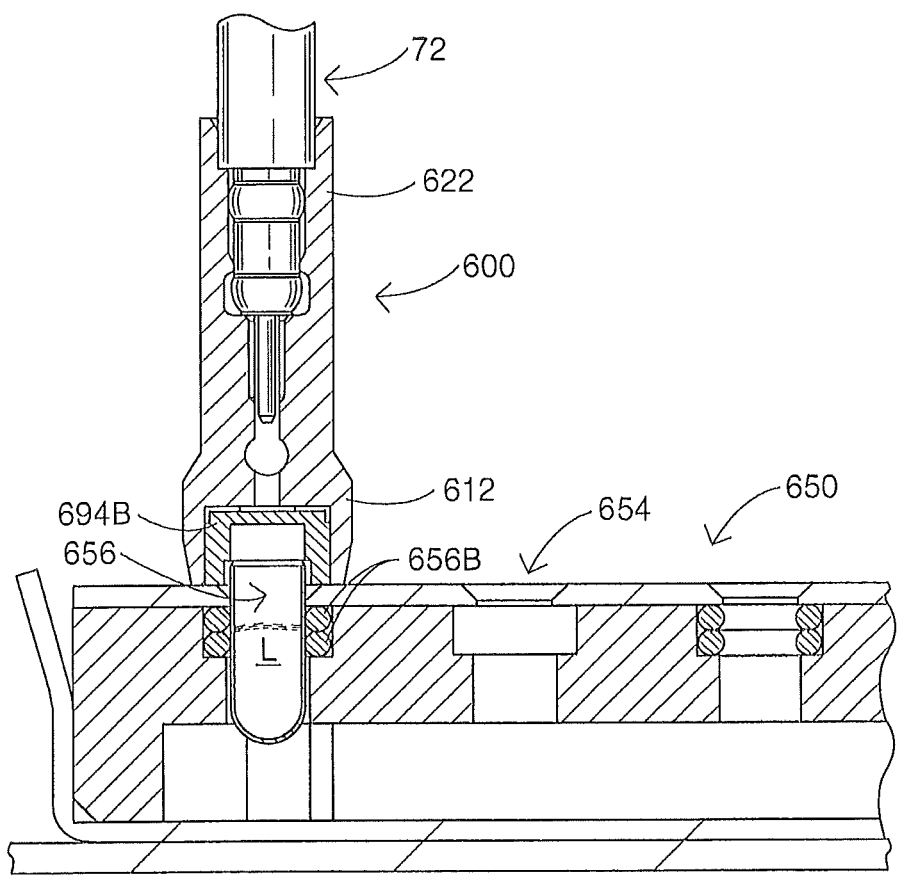
FIG. 24 is a cross-sectional view of the pipetting module, the lab member, the vial and the container rack taken along the line 22-22 of FIG. 21, but wherein the vial is positioned in a return slot of the container rack.

When desired, the vial 694 can be returned to the rack 650 (e.g., to a new location in the rack 650) or another rack or holder. In order to return the vial 694 to the rack 650, the controller 30 moves the pipetting module 60 to align the pipettor 72 (and thereby the vial 694) with a selected slot 656, and extends the pipettor 72 to insert the vial 694 into the slot 656 as shown in FIG. 24. The gripping elements 656B applying a gripping force $F_{S2}$ to the vial 694. The controller 30 then retracts the pipettor 72. The resistance force $F_{R2}$ imparted by the vial 694 (where the resistance force $F_{R2}$ includes the weight load $F_W$, and the grip force $F_{S2}$) is greater than the head-to-cap gripping force $F_G$, so that the vial 694 remains seated in the slot 656 as the pipettor 72 with the lab member 600 is pulled away.

The pipettor 72 (or another of the pipettors 74, 76, 78) and the lab member 600 can thereafter be used to grab and transport additional vials 694. When the lab member 600 is no longer needed, the controller 30 can move the pipetting module 60 and the pipettor 72 to return the lab member 600 to the holder slot 642 and disengage and release the lab member 600 from the pipettor 72 using the ejector sleeve 84 as described above with regard to the lab member 400 (FIG. 12).

While certain tools have been described and illustrated herein, other tools and devices can be integrated with adapter structures to form a lab member according to embodiments of the invention and manipulated as described. Other such tools may include, for example, piercing tools.

While certain lab members (e.g., the lab member 600) have been described herein for releasably engaging, transporting and releasing a solid workpiece such as a vial (e.g., the vials 694), lab members according to embodiments can be configured and used to releasably hold and configure other types and configurations of solid workpieces or objects. Other such solid workpieces may include, for example, lids, caps, racks, plates, manifold assemblies, and reagent troughs.

According to some embodiments and as illustrated by each of the embodiments depicted in the drawings, the adapter structures (e.g., adapter structures 122, 124, 126, 128) are configured relative to the associated pipettors (e.g., the pipettors 72, 74, 76, 78) such that the tips (e.g., the tips 82C) of the pipettors do not contact the adapter structures when the pipettors are inserted in the adapter structures.

While pipetting modules 60, 61 having four and eight pipettors have been described above, embodiments of the invention may include or be adapted for use with pipetting modules having any suitable number of pipettors. Fewer than all of the pipettors of a given pipetting module may be engaged with the lab member. For example, the pin tool lab member 400 (FIG. 12) can be used with a pipetting module having only a single pipettor or with a desired pipettor of a multi-pipettor pipetting module (e.g., module 60 (FIG. 1) or 61 (FIG. 10)). By way of further example, the eight-pipettor pipetting module 61 may be used to carry the four-adapter structure lab member 100 using four selected ones of the pipettors 72, 73, 74, 75, 76, 78, 79. The number and arrangement or configuration of the adapter structures may be modified as desired. For example, the adapter array 220 of the lab member 200 (FIG. 10) may be revised so that primary adapter structures are located on the extreme ends of the array and the interior adapter structures are secondary adapter structures. Similarly, the adapter array 120 (FIG. 3) may be modified so that the positions of the primary adapter structure 122 and the secondary adapter structure 124 are reversed. It will be appreciated that the foregoing examples are not exhaustive, and various other configurations may be provided.

Lab members, systems and methods according to embodiments of the invention can enable a pipettor to be used to pick up, move, assemble, disassemble, and/or release solid objects in a programmable method. These capabilities can be provided without the requirement of a separate, dedicated gripper instrument/device. The cost and space requirements associated with such gripper instruments/devices can thereby be avoided. The adapter structures can be configured to permit easily programmable or executable methods for attaching the lab members to the pipettors and releasing the lab members from the pipettors. The system can be scalable or expandable in that the adapter structures can be integrated with any suitable device or apparatus.

As noted above, operations described herein can be executed by or through the controller 30. The motors 54, 56, 58 and other devices of the pipetting module 60 and/or the liquid handler 40 can be electronically controlled. According to some embodiments, the controller 30 programmatically executes some, and in some embodiments all, of the steps described. According to some embodiments, the movement of the pipetting module 60 to pick up, move and release the lab member is fully automatically and programmatically executed by the controller 30.

The controller 30 may be any suitable device for providing the functionality described herein. According to some embodiments, the controller 120 is an appropriately configured microprocessor-based personal computer.

Embodiments of the controller 30 logic may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, controller 30 logic may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Figure 25:
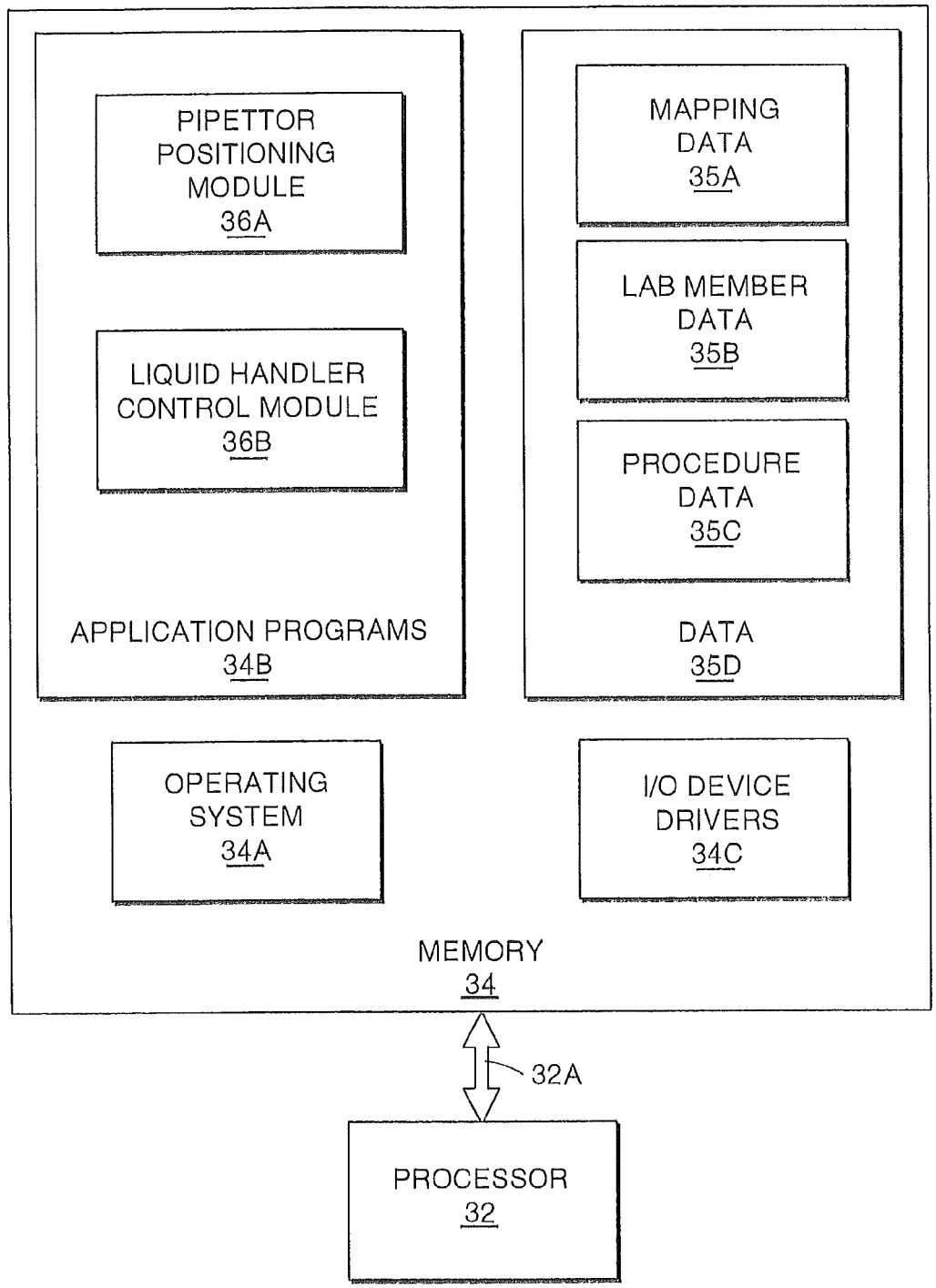
FIG. 25 is block diagram representing a controller forming a part of the laboratory liquid handling system of FIG. 1.

FIG. 25 is a schematic illustration of a circuit or data processing system that can be used in the controller 30. The circuits and/or data processing systems may be incorporated in a digital signal processor 32 in any suitable device or devices. The processor 32 communicates with the HMI 33 and memory 34 via an address/data bus 32A. The processor 32 can be any commercially available or custom microprocessor. The memory 34 is representative of the overall hierarchy of memory devices containing the software and data used to implement the functionality of the data processing system. The memory 34 can include, but is not limited to, the following types of devices: cache, ROM, PROM, EPROM, EEPROM, flash memory, SRAM, and DRAM.

FIG. 25 illustrates that the memory 34 may include several categories of software and data used in the data processing system: the operating system 34A; the application programs 34B; the input/output (I/O) device drivers 34C; and data 34D. The data 34D can include equipment-specific data. FIG. 25 also illustrates that the data 34D can include mapping data 35A, lab member data 35B, and procedure data 35C. FIG. 25 also illustrates that application programs 35B can include a pipettor positioning module 36A and a liquid handler control module 36B. The mapping data 35A can include data representing the positions (e.g., X, Y and Z coordinates) of objects or components in the work space of the system 10, 11. The lab member data 35B can include data representing characteristics of a lab member or lab members (e.g., lab members 100, 200, 300, 400, 500 and/or 600). The procedure data 35C can include data representing a protocol or sequence of steps to execute the procedures described herein. The pipettor positioning module 36A can be used to control the motors 54, 56, 58, for example, to position and reposition the pipetting module 60, the pipettors 72-78, and the ejector sleeves 84. The liquid handler control module 36B can be used to control actuation of the liquid handler 40 to aspirate and/or dispense fluid.

As will be appreciated by those of skill in the art, the operating system 34A may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 34C typically include software routines accessed through the operating system 34A by the application programs 34B to communicate with devices such as I/O data port(s), data storage and certain memory components. The application programs 34B are illustrative of the programs that implement the various features of the data processing system and can include at least one application, which supports operations according to embodiments of the present invention. Finally, the data 34D represents the static and dynamic data used by the application programs 34B, the operating system 34A, the I/O device drivers 34C, and other software programs that may reside in the memory 34.

As will be appreciated by those of skill in the art, other configurations may also be utilized while still benefiting from the teachings of the present invention. For example, one or more of the modules 36A-B may be incorporated into the operating system, the I/O device drivers or other such logical division of the data processing system. Thus, the present invention should not be construed as limited to the configuration of FIG. 25, which is intended to encompass any configuration capable of carrying out the operations described herein. Further, one or more of the modules can communicate with or be incorporated totally or partially in other components, such as the controller 30.

Figure 26:
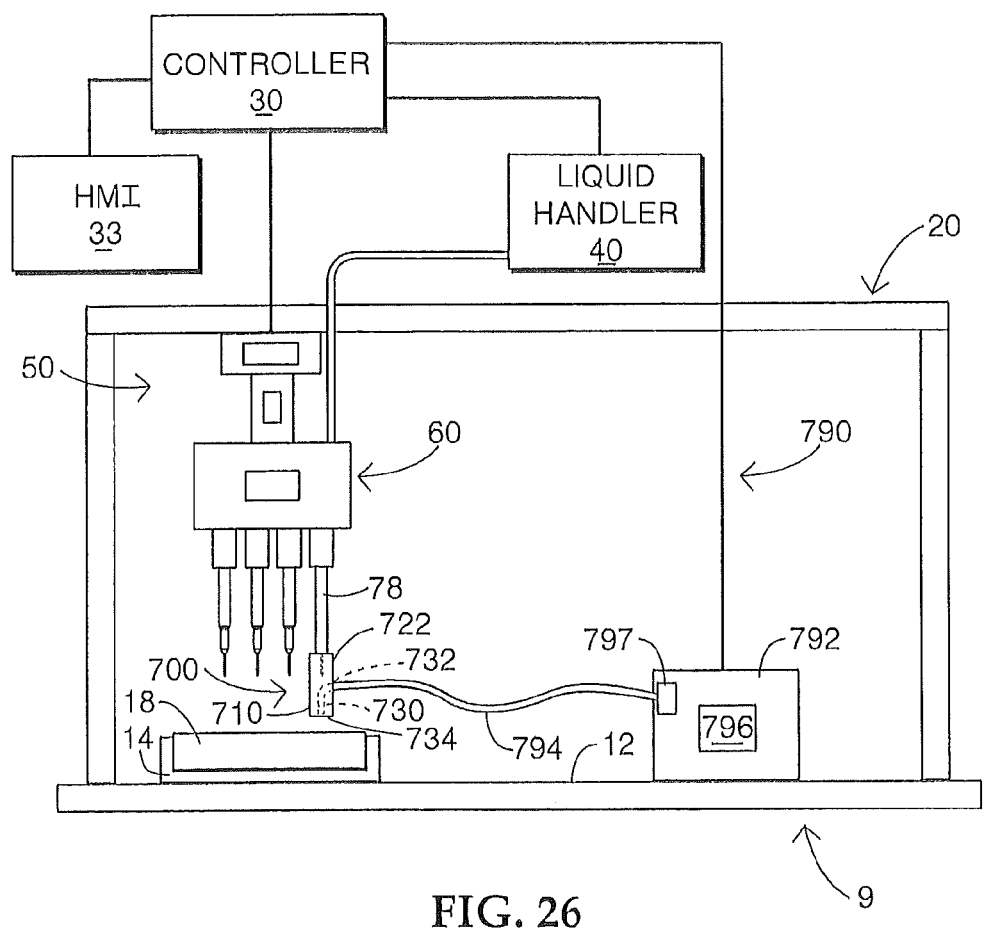
FIG. 26 is a schematic diagram of a laboratory liquid handling system according to further embodiments of the invention.

With reference to FIG. 26, a liquid handling system 9 according to further embodiments of the present invention is shown therein. In FIG. 26 and the description that follows, like reference numerals refer to corresponding components as referred to above with regard to the system 10.

The system 9 includes an auxiliary flowable material handling system 790. The system 790 includes a material handler 792, a lab member 700, and a length of tubing 794 (e.g., flexible tubing) extending between the material handler 792 and the lab member 700 to provide fluid communication therebetween.

The material handler 792 may be any suitable device that can aspirate or dispense a desired amount of material. According to some embodiments, the material handler 792 is adapted to aspirate and/or dispense a liquid. According to some embodiments, the material handler 792 is adapted to aspirate or dispense a powder. In some embodiments, the material handler 792 includes a pump 796 and, in some embodiments, a peristaltic pump. In some embodiments, the material handler 792 includes a vacuum manifold fluidly connected to a vacuum source. The pump 796 and/or a valve or valves 797 or the like may be electronically controlled by a controller such as the controller 30, for example. According to some embodiments, the material handler 792 is controlled independently of the liquid handler 40.

The lab member 700 includes an adapter structure 722 and a body or nozzle 710. The lab member 700 may be monolithic or integrally formed. The lab member 700 may be formed of the same materials and in the same manner as described for the lab member 600.

The adapter structure 722 may be constructed and configured in the same manner as described herein for the adapter structure 222 or the adapter structure 622, for example.

The nozzle 710 has a through passage 730 defined therein and fluidly connecting a first port 732 and an opposed second port 734. The first port 732 is coupled to an end of the tubing 794 and the second port 734 is open.

In use, in accordance with methods of the present invention, the liquid handling system 9 can be used to dispense or aspirate material to or from a container 18, for example. The lab member 700 is releasably engaged and carried by a pipettor 78 of the pipetting module 60 as described herein to selectively position the second port 734 relative to the container 18. The material handler 792 can then be actuated to aspirate material (e.g., liquid) from the container 18 or dispense material (e.g., liquid or powder) into the container 18 through the tubing 794, the port 732, the passage 730 and the port 734. According to some embodiments and as illustrated, this material follows a flow path separate from the flow path of liquid aspirated or dispensed through the pipettors 72, 74, 76 and 78.

According to some embodiments, an adapter structure as disclosed herein can be used to transmit electrical current between a pipettor and a lab object integrated with the adapter structure or an object, mass or volume separate from the adapter structure. For this purpose, at least a portion of the adapter structure is formed of an electrically conductive material and the adapter structure has an electrical contact portion to engage and electrically couple with an inserted pipettor. The electrically conductive material can provide electrical continuity between a controller and/or power supply on the pipetting module (e.g., the pipetting module 60) and/or a controller and/or power supply connected thereto (e.g., the controller 30) and a controller and/or power consuming device forming a part of a lab member or module (e.g., the lab member 500) mounted on the pipettors of the pipetting module by the adapter structure(s). According to some embodiments, the electrically conductive material is metal or an electrically conductive polymer, such as a polymer filled or coated with carbon black or metallic particles. The adapter structure may be fitted with an electrically conductive contact sleeve. By way of example, the lab member 500 (FIG. 13) is illustratively provided with electrically conductive sleeves 515 to provide electrical continuity between the pipettors 72, 78 and the sensor module 512 for transmission of power and/or data signals as discussed below.

According to some embodiments, the electrically conductive lab member enables liquid level sensing. By way of example, the system 10 and the pipettor 72 may be provided with a capacitive liquid level sensor system as disclosed in U.S. Pat. No. 7,191,647 to Harazin et al. and/or U.S. Pat. No. 5,365,783 to Zweifel, the disclosures of which are incorporated herein in their entireties. The lab member 400 (FIG. 12) can be formed of metal (or another suitable electrically conductive material) to provide electrical continuity between the lower section 80F of the pipettor shaft 80 and the pin tool 410. In this manner, the pin tool 410 becomes an extension of the pipettor shaft 80 and serves as a probe in the same manner as the pipettor probes as described in the aforementioned patents. Capacitance formed between the pin tool 410 and the liquid can be monitored by a capacitance sensor circuit electrically coupled to the pipettor shaft 72, for example.

According to some embodiments, the electrically conductive lab member provides a supply of power to a device. By way of example, one or more of the adapter structures of the adapter structure array 520 (FIG. 13) of the lab member 500 can be electrically conductive and configured to transmit power to the sensor module 512 from one or more of the pipettors 72, 74, 76, 78 (e.g., via the pipettor shaft or shafts 80 thereof) to enable the sensor module 512 to operate.

According to some embodiments, the controller 30 communicates with a device mounted on one or more pipettors using data signals transmitted through the pipettor(s). For example, in some embodiments, an electrically conductive circuit is formed between the sensor module 512 (FIG. 13) and the controller 30 by the adapter array 520 and one or more of the pipettor shafts 72, 74, 76, 78. In some embodiments, the data signals are carried over a power supply loop (i.e., a loop providing operational power to the sensor device 512) and are embodied in a different frequency to enable a data communication circuit to detect, distinguish and process the data signals. The data may be superimposed over the power signal by a capacitive coupling.

Figure 27:
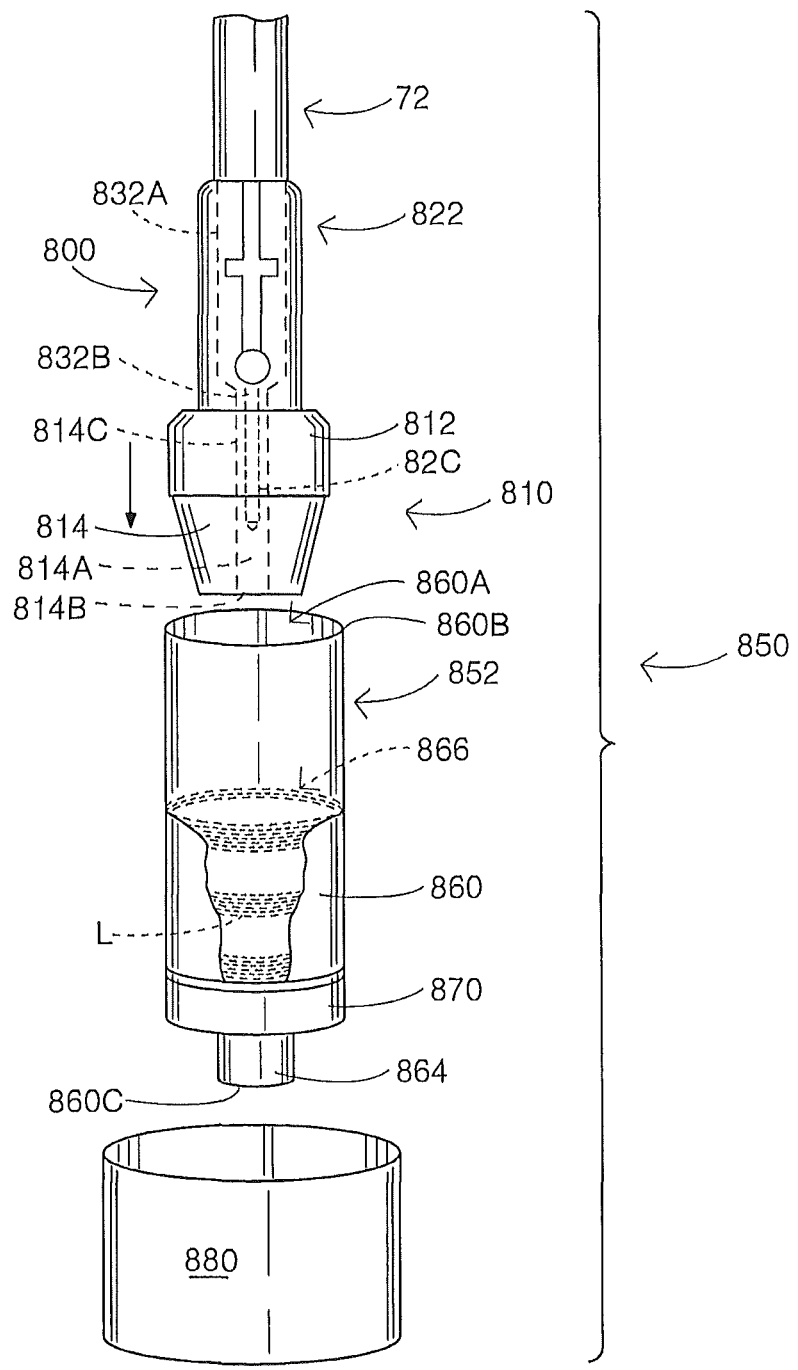
FIG. 27 is a fragmentary view of a pressure filtration system according to further embodiments of the invention.

With reference to FIG. 27, a pressure filtration system 850 according to further embodiments of the present invention is shown therein. The system 850 includes a lab member 800 according to embodiments of the invention mounted on the pipettor 72. The lab member 800 can be engaged, transported and ejected or released from the pipettor 72 as described herein with reference to the pin tool lab member 400 (FIG. 13), for example.

The lab member 800 includes a stopper 810 and an integral adapter structure 822. The adapter structure 822 corresponds to the adapter structure 622 of the lab member 600 (FIG. 15). The stopper 810 includes a base 812 and a gasket 814. The gasket 814 may be formed of a suitable resilient sealing material such as rubber, and may be adhered or otherwise affixed to the base 812. The base 812 may be integrally molded with the adapter structure 822.

A through passage 814A is defined in the gasket 814 and terminated at an outlet 814B and an inlet 814C. According to some embodiments, the gasket 814 is frusto-conical with a taper in a downward direction as illustrated. In addition to the socket 832A (corresponding to the socket 632A; FIG. 17), a passage 832B extends through the lab member 800 from the socket 832A to the gasket inlet 814C.

The pressure filtration system 850 further includes a container assembly 852 configured to hold a volume of liquid L to be filtered. The container assembly 852 may be a well of single filter column or well (e.g., one column of a multi-well plate). The container assembly 852 includes a vessel 860 defining a chamber 866. The vessel 860 includes an upper edge 860A defining a top opening 860B. An outlet 860C is located in a bottom wall 862 of the vessel 860 and may pass through an integral nozzle 864. A filter bed 870 is disposed on the bottom wall 862 between the opening 860B and the outlet 860C. A capture plate or tube 880 may be provided below the nozzle 864.

In use and according to method embodiments of the invention, the lab member 800 is mounted on the pipettor 72 such that the adapter structure 822 releasably engages and couples the lab member 800 to the pipettor shaft 80, and the pipettor 72 forms a substantially airtight seal with the lab member 800. The tip 82C of the pipettor 72 extends into the passage 814A of the gasket 814.

The pipetting module 60 is operated to align the stopper 810 with the top opening 860B of the vessel 860. The pipettor 72 is thereafter extended downwardly to force the stopper 810 into sealing engagement with the vessel opening 860B. More particularly, the gasket 814 engages the upper edge 860A to form an airtight, pressure resistant seal.

The liquid handler 40 is then operated to force positively pressurized air through the pipettor 72 and the gasket passage 814A into the vessel 860 (e.g., using a syringe). The pressurized air in turn forces the liquid L out of the chamber 866 through the filter bed 870 and the outlet 860C. Solids or other desired materials are thereby captured in the filter bed 870 and the filtered liquid is captured in the capture plate or tube 880.

While only a single lab member 800 and container assembly 852 are shown and described above, two or more lab members 800 may be mounted on respective ones of the pipettors 72, 74, 76, 78, for example, used to engage respective container assemblies 852, and used to push liquid volumes through the filters of the container assemblies 852. According to some embodiments, the pipettors are simultaneously pressurized to effect the filtering procedure.

Figure 28:
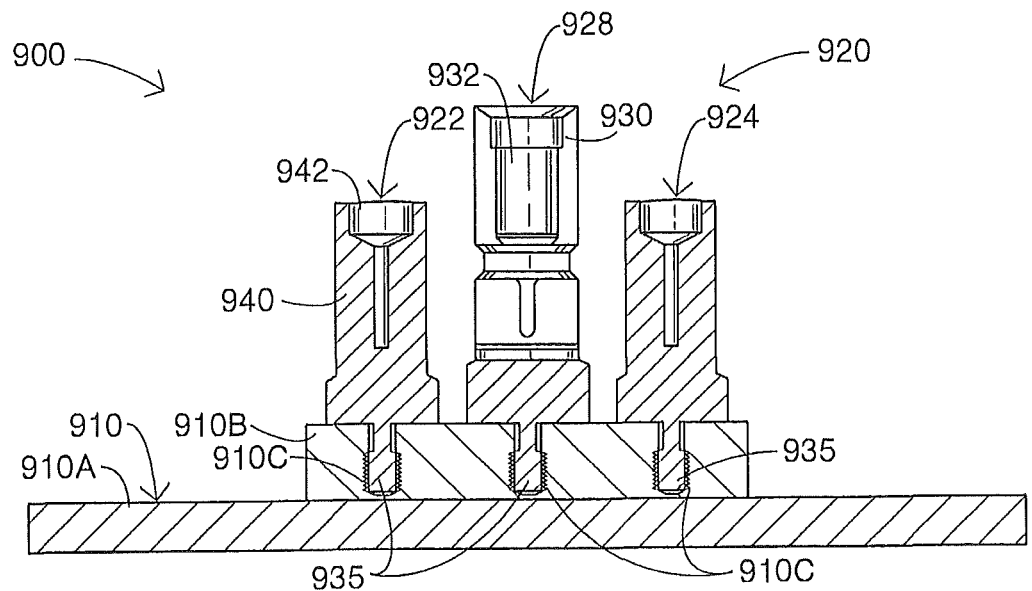
FIG. 28 is a cross-sectional view of a lab member according to further embodiments of the invention.
Figure 29:
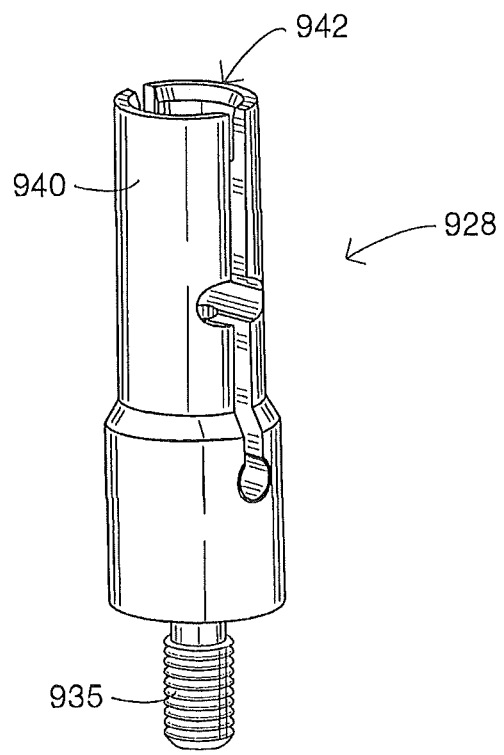
FIG. 29 is a perspective view of a primary adapter member forming a part of the lab member of FIG. 28.

With reference to FIGS. 28 and 29, a lab member 900 according to further embodiments of the present invention is shown therein. The lab member 900 can be used with the pipetting module 60 in the same manner as described above with regard to the lab member 100. The lab member 900 corresponds to the lab member 100 except that the lab member 900 includes an adapter array 920 that is releasably or removably and reconnectably coupled to a lid member 910.

The adapter array 920 includes a primary adapter member 928 and a pair of secondary adapter members 922 and 924 corresponding to adapter structures 128, 122 and 124 (FIG. 2), respectively. Each secondary adapter member 922, 924 includes a body 940 defining a pipettor socket 942. The primary adapter member 928 includes a body 930 defining a pipettor socket 932. The adapter members 922, 928, 924 differ from the adapter structures 122, 128, 124 in that the adapter members 922, 928, 924 each include a coupling feature in the form of an externally threaded post 935.

The lid member 910 includes a lid body 910A and a mounting bar 910B secured to the top of the lid body 910A (e.g., by adhesive, welding or fasteners). Coupling features in the form of internally threaded bores 910C are provided in the mounting bar 910B.

In use, the posts 935 of the adapter members 922, 928 and 924 can be screwed into the bores 910C to rigidly secure the adapter members 922, 928 and 924 to the lid member 910 so that the adapter members 922, 928, 924 are integral with the lid member 910. The adapter members 922, 928 and 924 can thereafter be used in the same manner as described above for the adapter structures 122, 128 and 124 to engage, transport and release the lab member 900.

The provision of removable and reconnectable adapter members 922, 928 and 924 may provide certain advantages. The adapter members 922, 928 and 924 can be removed and then mounted interchangeably on another lab member/object or lab members/objects (likewise having mounting bores corresponding to the mounting bores 910C). If desired, the adapter members 922, 928 and 924 (or other suitably configured adapter members) can be mounted or remounted on the lid member 910 to again permit manipulation of the lid member 910 as described. This flexibility can enable the operator to configure the adapter array as desired for the task (e.g., by selecting the combination of primary and secondary adapters employed on a lab member). The flexibility can also reduce or eliminate the need to provide each lab member with a dedicated adapter array, which may add significant cost.

While the lab member 900 uses a threaded post and cooperating bore for releasably coupling the adapter members 922, 928 and 924 to the lid member 910, other coupling mechanisms may be used in accordance with embodiments of the invention.

Figure 30:
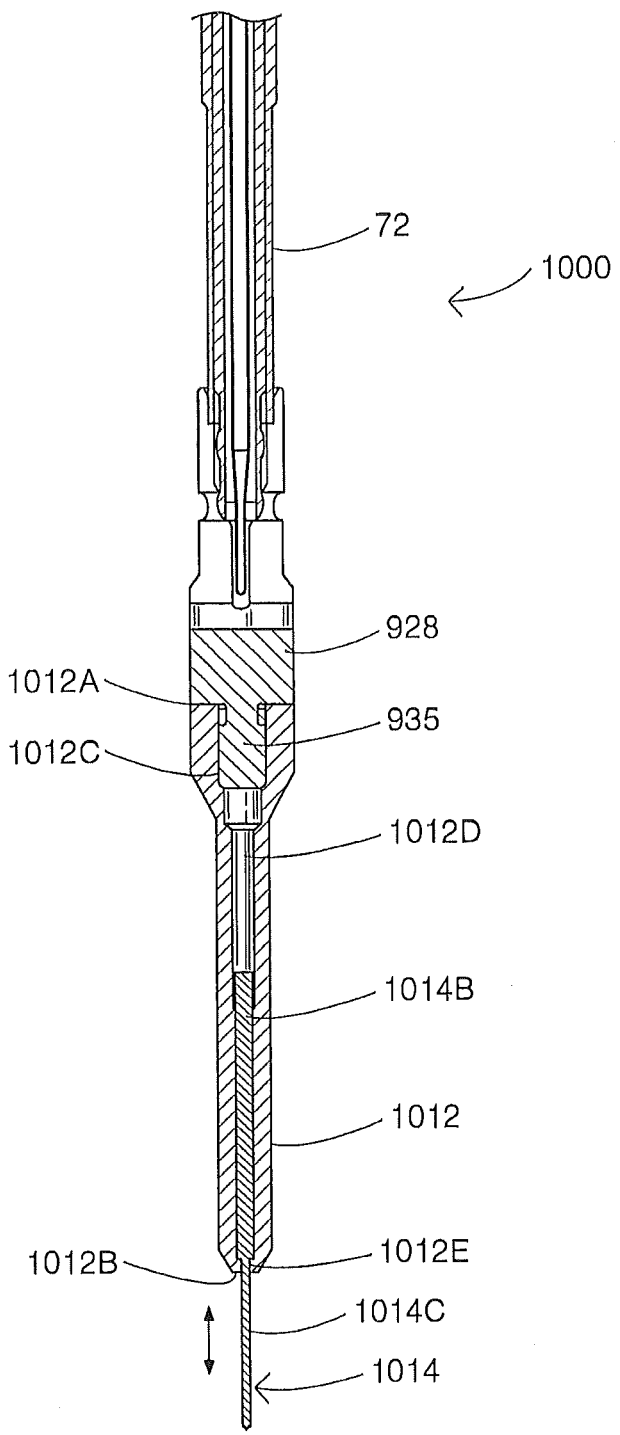
FIG. 30 is a cross-sectional view of a lab member according to further embodiments of the invention.

With reference to FIG. 30, a lab member 1000 according to further embodiments of the invention is shown therein mounted on the pipettor 72. For the purpose of illustration, the remainder of the pipetting module 60, other than the actuator assembly 72A, is not shown in FIG. 30.

The lab member 1000 includes a multi-piece lab tool in the form of a pin tool 1010, and the removable and reconnectable adapter structure 928 (FIG. 29). The lab member 1000 may employ an adapter structure other than the adapter structure 928, which is shown in order to illustrate that the adapter member 928 may be re-used with multiple different lab objects or tools. Alternatively, the lab member 1000 may include an integral adapter structure corresponding to the integral adapter structure 422 (FIG. 12).

The pin tool 1010 includes a floating pin member or tip 1014 and a body or shaft member 1012. The body member 1012 has opposed ends 1012A, 1012B, and a threaded bore 1012C in the end 1012A, and defines an axially extending upper slot 1012D and an axially extending lower slot 1012E. The diameter of the lower slot 1012E is less than that of the upper slot 1012D.

The threaded post 935 of the adapter member 928 is mounted in the bore 1012C. The pin member 1014 is slidably seated in the slots 1012D, 1012E and extends from the end 1012B. More particularly, the pin member 1014 has an enlarged head portion 1014B that is able to slide in the upper slot 1012D but is unable to slide through the lower slot 1012E.

The lab member 1000 can be used in the same manner as the pin tool 400 (FIG. 12) in accordance with embodiments of the present invention. In use, the pin member 1014 is able to "float" with respect to the shaft member 1012. For example, in the event the pin member 1014 is lowered into a container and hits a solid surface, the pin member 1014 will slide up the slots 1012D, 1012E into the shaft member 1012 to prevent damage.

Figure 31:
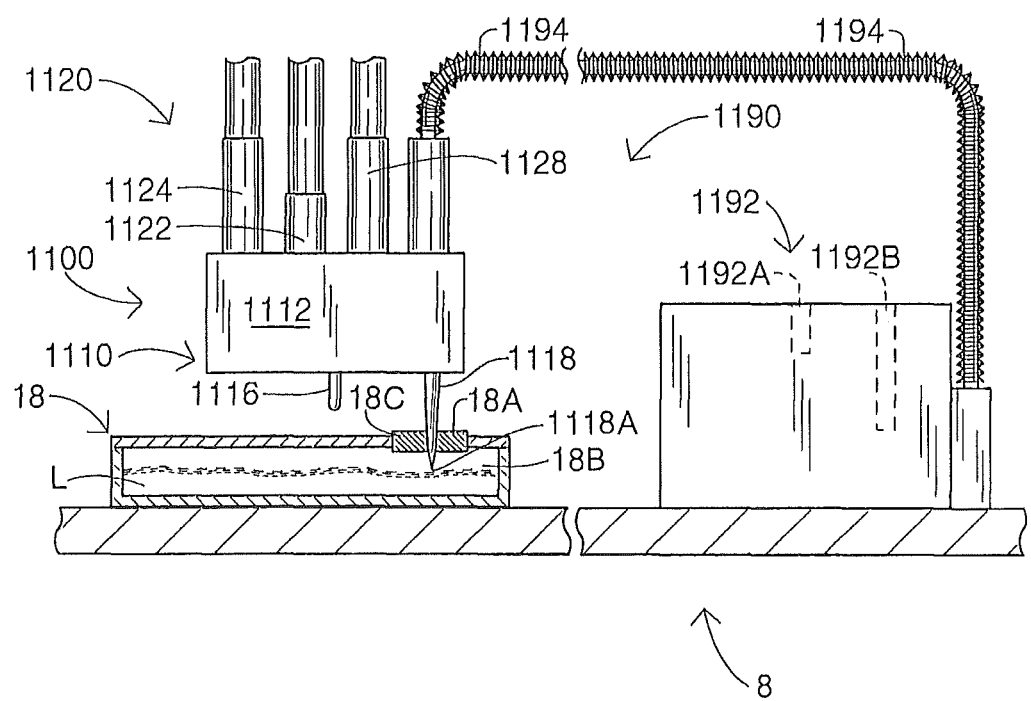
FIG. 31 is a fragmentary view of a laboratory liquid handling system according to further embodiments of the invention.

With reference to FIG. 31, a liquid handling system 8 according to further embodiments of the present invention is shown therein. The system 8 corresponds to the liquid handling system 9 (FIG. 26), except as follows.

The system 8 includes an auxiliary flowable material handling system 1190. The system 1190 corresponds generally to the system 790 and includes a material handler 1192, a lab member 1100, and a length of tubing 1194 (e.g., flexible tubing) extending between the material handler 1192 and the lab member 1100 to provide fluid communication therebetween.

The illustrated lab member 1100 includes a dispensing head 1110 including a body 1112 and an array 1120 of removable and reconnectable adapter structures 1124, 1122, 1128. However, it will be appreciated that an integral adapter structure or structures may be provided instead. A locator structure 1116 extends from the bottom of the body 1112.

The tubing 1194 is connected through the body 1112 to a tip, pin nozzle or cannula 1118. The cannula 1118 may be formed of a rigid metal such as stainless steel. The cannula 1118 extends downwardly from the body 1112 to a tip 1118A and has a lumen extending therethrough and in communication with each of the tubing 1194 and an outlet at the tip 1118A.

In use, in accordance with methods of the present invention, the liquid handling system 8 can be used to dispense or aspirate material to or from a sealed flask or container 18, for example, in the same manner as described above with respect to the system 9 (FIG. 26), except as follows. The cannula 1118 is configured (e.g., with a relatively sharp tip 1118A) to permit the cannula 1118 to pierce and penetrate through a septa 18A (e.g., a septa cap or mat (formed of silicone, for example)) covering a port 18C communicating with a well 18B of the container 18, and to be withdrawn therefrom, without displacing or compromising the seal of the septa 18A following removal of the cannula 1118.

The material handler 1190 may serve as a docking station for the lab member 1100 or a further structure may be provided to serve as a docking station. A slot 1192A is provided in the material handler 1190 or other docking station to receive the locator post 1116 and thereby positively position the docked lab member 1100. A slot 1192B is also provided in the material handler 1190 or other docking station to receive the cannula 1118. The docking station may be provided with a washing system and/or a flushing system operable to sanitize the tubing 1194 and/or the cannula 1118.

According to some embodiments, the system 8 includes a plurality of the lab members 1100 and associated material handlers and docking stations.

Figure 32:
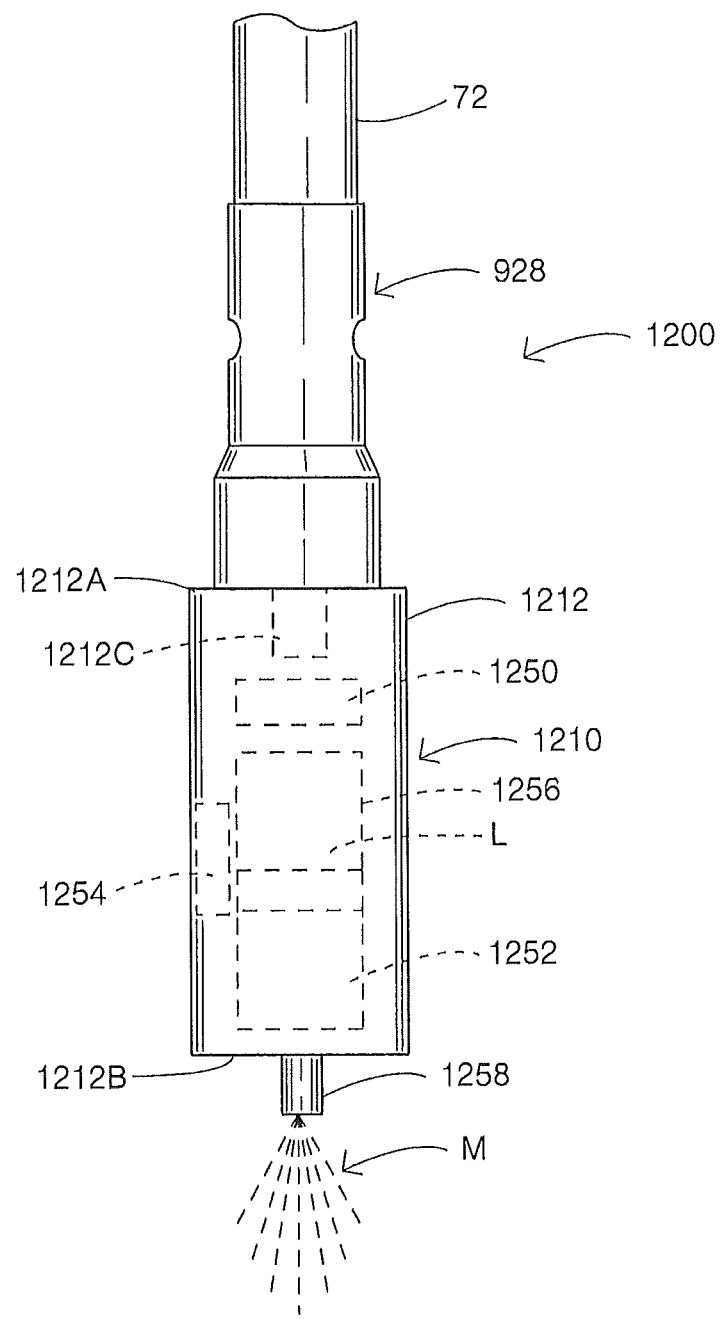
FIG. 32 is a side view of a lab member according to further embodiments of the invention including an atomizer

With reference to FIG. 32, a lab member 1200 according to further embodiments of the invention is shown therein mounted on the pipettor 72. For the purpose of illustration, the remainder of the pipetting module 60, other than the actuator assembly 72A, is not shown in FIG. 32.

The lab member 1200 includes an atomizer module 1210, and the removable and reconnectable adapter structure 928 (FIG. 29). The lab member 1200 may employ an adapter structure other than the adapter structure 928, which is shown in order to illustrate that the adapter member 928 may be re-used with multiple different lab objects or tools. Alternatively, the lab member 1200 may include an integral adapter structure corresponding to the integral adapter structure 422 (FIG. 12).

The atomizer module 1210 includes a body or housing 1212 having opposed ends 1212A, 1212B, and a threaded bore 1212C in the end 1212A. The threaded post 935 of the adapter member 928 is mounted in the bore 1212C. To removably mount the atomizer module 1210 on the adapter member 928.

The atomizer module 1210 further includes an onboard controller 1250, a liquid atomizing mechanism 1252, a battery 1254, and a container 1256 mounted in the housing 1212. A spray nozzle 1258 extends from the lower end 1212B.

The container 1256 may be a replaceable and/or refillable cartridge and contains a supply of the liquid L to be dispensed. The container 1256 may be preloaded with the liquid L and sterilized prior to being installed in the atomizer module 1210. According to alternative embodiments, the liquid may be supplied to the atomizer module 1210 by supply tubing (e.g., the supply tubing 794; FIG. 26).

The atomizer mechanism 1252 may include an ultrasonic percussion device or a heating element (e.g., a fine metal filament) powered by the battery 1254. According to alternative embodiments, the liquid L may instead be atomized by forcing the liquid through a small orifice under high pressure (e.g., in the range of from about 0 to 100 ml/minute). The pressure and/or the pressurized liquid may be supplied through a supply line to the atomizer module 1210.

The battery 1254 may supply power to both the controller 1250 and the atomizer mechanism 1252. In some embodiments, the controller 1250 and/or the atomizer mechanism 1252 are powered by a remote power source through the pipettor 72 and the adapter member 928 as discussed above with regard to the lab member 500 (FIG. 13). In some embodiments, the controller 1250 and/or the atomizer mechanism 1252 are powered by a remote power source via a separate power line.

The lab member 1200 may be used in generally the same manner as the lab member 700 (FIG. 26) in accordance with embodiments of the present invention. In use, the atomizer mechanism 1252 atomizes a prescribed quantity of the liquid L from the container 1256 and dispenses or ejects the atomized liquid as a fine vapor or mist M from the nozzle 1258. The mist M contains micro-size droplets of the liquid. According to some embodiments, the droplets have an average size in the range of from about 10 to 40 microns.

Figure 33:
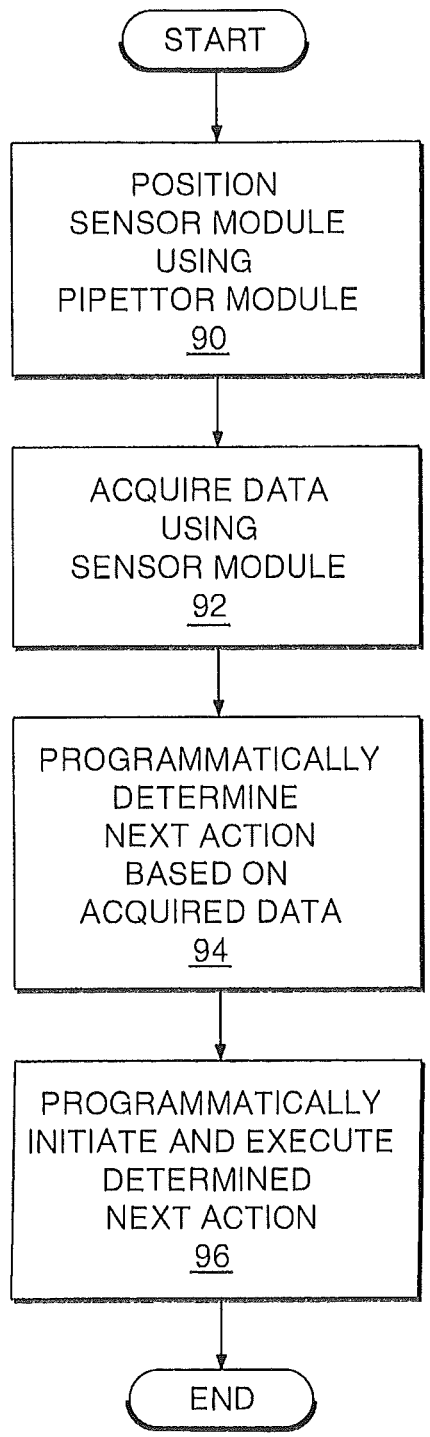
FIG. 33 is a flow chart representing methods according to embodiments of the invention.

With reference to FIG. 33, operations for using a liquid handling system as described herein may include intelligent decision making using data acquired by a lab member as disclosed herein. According to some embodiments, a detector or sensor lab member is transported by a pipetting module and positioned thereby in a selected or desired location (Block 90). The sensor lab member is then used to acquire data by sensing at the selected location (Block 92). Based on the data acquired, a controller of the liquid handling system programmatically determines whether to take action and/or what step or action to execute next (Block 94). The determined or selected action may then be initiated and executed programmatically by the controller (Block 96).

In some embodiments, the liquid handling system engages a first, sensor lab member with a pipetting module and transports the sensor lab member thereby to a location proximate a sample or object. The sensor lab member is then used to sense or detect an attribute or characteristic of the sample or object, and a data signal corresponding to or representing the detected attribute or characteristic is generated by the sensor lab member and sent to the controller. The controller then determines what action to take. If selected by the controller, the first pipetting module or a further pipetting module is used to engage a second lab member and to transport the second lab member to a suitable location where the second lab member is used to execute a further step deemed necessary or appropriate in view of the data provided by the detector lab member.

By way of example, the liquid handling system may be the system 9 (FIG. 26) and the first lab member may be the lab member 500 (FIG. 13). The lab member 500 is picked up (if necessary) and transported to the container 18 by the pipetting module 60. The lab member 500 is used to detect or sense a prescribed attribute of a sample at a selected trough in the container 18 such as the presence/absence, height or volume of the sample. If the detected volume is lower or higher than desired, the controller 30 will pick up (if necessary) and transport the lab member 700 to the container 18. The controller 30 may use a second pipetting module, or may release the lab member 500 from the pipetting module 60 and pick up the lab member 700 using the pipetting module 60. Once positioned, the lab member 700 is used to dispense material into or aspirate material from the selected trough to bring the sample volume into the desired range. In some embodiments, the lab member 500 may be used to detect the fill level of multiple troughs and the controller 30 may thereafter add material (using the lab member 700) to the troughs having low fill levels while skipping the troughs having adequate fill levels.

It will be appreciated that various other attributes can be detected and acted on in other ways. For example, the detector lab member may sense and report a temperature, color, or other attribute of the sample and the controller may respond accordingly by moving the container to a warmer or chiller (using the lab member 200 (FIG. 10), for example) or selecting and adding a corrective material to the trough different from the material of the sample.

In further embodiments, the system could use a suitable sensor module lab member (e.g., a scanner or camera module) mounted on and transported by the pipetting module to scan for objects on the lab deck. For example, the system could use the sensor module to scan for objects or liquids on the deck to programmatically confirm (using the controller) that all objects/liquids are in the correct locations or detect objects that are in incorrect locations.

While lab members including sensor modules (e.g., the lab member 500) and an atomizer (e.g., the lab member 1200) have been described herein, embodiments of the invention may include lab members having other types of electronics modules and one or more integral adapter structures (e.g., adapter structures 122, 124, 126, 128 or adapter members 922, 928, 924) may be provided. Such electronics modules may include on-board controllers, power supplies, and/or other electrical circuit components, and may be connected to the pipetting module to enable transmission of power and/or communications signals through the adapter structure(s).

Lab members having integral adapter structures in accordance with the present invention may be used or incorporated in any suitable laboratory liquid handling system. Suitable systems may include the JANUS™ Automated Workstation with any appropriate Pipetting Arm such as a Varispan™ Pipetting Arm equipped with VersaTip™ pipettors, for example.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A laboratory liquid handling system comprising:
   a pipetting module including a pipettor including a pipettor shaft and a pipetting tip extending from an end of the pipettor shaft;
   a lab member including:
      an electronics module; and
      an integral adapter structure, wherein the integral adapter structure is configured to releasably secure the lab member to the pipettor shaft; and
   a drive system including a motor and a controller operative to control the motor, wherein the drive system includes a controller programmed to:
      selectively engage the pipettor shaft with the integral adapter structure to secure the lab member to the pipetting module;
      move the pipetting module to transport the lab member secured to the pipetting module; and
      selectively disengage the pipettor shaft from the integral adapter structure to thereby release the lab member from the pipetting module.

2. The laboratory liquid handling system of claim 1 wherein the electronics module includes a transducer.

3. The laboratory liquid handling system of claim 2 wherein the electronics module includes a housing holding the transducer.

4. The laboratory liquid handling system of claim 1 wherein the electronics module includes an onboard controller.

5. The laboratory liquid handling system of claim 1 wherein the electronics module includes a sensor.

6. The laboratory liquid handling system of claim 5 wherein the sensor is an ultrasonic sensor.

7. The laboratory liquid handling system of claim 5 wherein the sensor is an optical sensor.

8. The laboratory liquid handling system of claim 5 wherein the sensor is a temperature sensor.

9. The laboratory liquid handling system of claim 1 wherein the lab member is includes an electrically conductive material to transmit power and/or communications signals through the integral adapter structure to and/or from the electronics module.

10. The laboratory liquid handling system of claim 9 wherein the integral adapter structure includes an electrical contact portion to engage and electrically couple the electrically conductive material with a portion of the pipettor when the pipettor is inserted into the integral adapter structure.

11. The laboratory liquid handling system of claim 10 wherein the integral adapter structure includes an electrically conductive sleeve configured to receive the pipettor and provide electrical continuity between the pipettor and the electronics module.

12. The laboratory liquid handling system of claim 1 wherein the lab member further includes a second integral adapter structure configured to engage a second pipettor shaft of the pipetting module.

13. The laboratory liquid handling system of claim 1 wherein the integral adapter structure includes a socket configured to receive the pipetting tip and an adjacent lower section of the pipettor shaft such that the lower section is releasably captured in the socket.

14. A method for transporting a lab member using a laboratory liquid handling system including a pipetting module and a drive system, the pipetting module including a pipettor including a pipettor shaft and a pipetting tip extending from an end of the pipettor shaft, the method comprising:
   providing a lab member including:
      an electronics module; and
      an integral adapter structure, wherein the integral adapter structure is configured to releasably secure the lab member to the pipettor shaft;

using the drive system, selectively engaging the pipettor shaft with the adapter structure to secure the lab member to the pipetting module;

using the drive system, moving the pipetting module to transport the lab member secured to the pipetting module; and using the drive system, selectively disengaging the pipettor shaft from the integral adapter structure to thereby release the lab member from the pipetting module.

15. The method of claim 14 wherein:
the electronics module includes a sensor; and
the method further includes acquiring data from a selected location using the sensor coupled to the pipettor shaft.

16. The method of claim 15 further including:
using the sensor, sensing an attribute at the selected location and generating and sending a corresponding data signal to a controller; and
using the controller, programmatically determining a next action based on the data signal.

17. The method of claim 14 further including transmitting power through the integral adapter structure to and/or from the electronics module.

18. The method of claim 14 further including transmitting communications signals through the integral adapter structure to and/or from the electronics module.

19. The method of claim 14 wherein the electronics module includes a transducer.

20. The method of claim 19 wherein the electronics module includes:
a housing holding the transducer; and
an onboard controller.

21. The method of claim 14 wherein:
the lab member further includes a second integral adapter structure configured to engage a second pipettor shaft of the pipetting module; and
the method includes:
using the drive system, selectively engaging the second pipettor shaft with the second adapter structure td secure the lab member to the pipetting module; and
using the drive system, selectively disengaging the second pipettor shaft from the second integral adapter structure to thereby release the lab member from the pipetting module.

22. The method of claim 14 wherein:
the integral adapter structure includes a socket; and
the step of selectively engaging the pipettor shaft with the adapter structure includes inserting the pipetting tip and an adjacent lower section of the pipettor shaft into the socket such that the lower section is releasably captured in the socket.

* * * * *

UNITED STATES PATENT AND TRADEMARK OFFICE
CERTIFICATE OF CORRECTION

| | | |
|---|---|---|
| PATENT NO. | : 9,259,737 B2 | Page 1 of 1 |
| APPLICATION NO. | : 14/313467 | |
| DATED | : February 16, 2016 | |
| INVENTOR(S) | : Brady et al. | |

It is certified that error appears in the above-identified patent and that said Letters Patent is hereby corrected as shown below:

<u>In the Claims:</u>
Column 26, Claim 9, Line 35: Please correct "member is includes"
                                 to read -- member includes --

Column 28, Claim 21, Line 12: Please correct "structure td"
                                 to read -- structure to --

Signed and Sealed this
Twenty-third Day of August, 2016

Michelle K. Lee
*Director of the United States Patent and Trademark Office*